(12) United States Patent
Tempelman et al.

(10) Patent No.: US 12,070,383 B2
(45) Date of Patent: Aug. 27, 2024

(54) SYSTEM FOR GAS TREATMENT OF A CELL IMPLANT

(71) Applicant: Giner, Inc., Newton, MA (US)

(72) Inventors: Linda Tempelman, Lincoln, MA (US); Simon Stone, Arlington, MA (US); Klearchos Papas, Tucson, AZ (US)

(73) Assignee: GINER, INC., Newton, MA (US)

( * ) Notice: Subject to any disclaimer, the term of this patent is extended or adjusted under 35 U.S.C. 154(b) by 0 days.

(21) Appl. No.: 18/222,633

(22) Filed: Jul. 17, 2023

(65) Prior Publication Data

US 2024/0189088 A1  Jun. 13, 2024

Related U.S. Application Data

(63) Continuation of application No. 16/266,687, filed on Feb. 4, 2019, now Pat. No. 11,701,215, which is a continuation of application No. 14/495,644, filed on Sep. 24, 2014, now Pat. No. 10,231,817.

(60) Provisional application No. 61/881,654, filed on Sep. 24, 2013.

(51) Int. Cl.
| | |
|---|---|
| *A61F 2/02* | (2006.01) |
| *A61M 5/00* | (2006.01) |
| *A61M 5/142* | (2006.01) |
| *A61K 48/00* | (2006.01) |

(52) U.S. Cl.
CPC .......... *A61F 2/022* (2013.01); *A61K 48/0075* (2013.01); *A61M 2005/006* (2013.01); *A61M 2005/14204* (2013.01); *A61M 2202/0208* (2013.01); *A61M 2205/7536* (2013.01)

(58) Field of Classification Search
CPC ................ A61F 2/022; A61K 48/0075; A61M 2005/14204; A61M 2005/006; A61M 2202/0208; A61M 2205/7536
See application file for complete search history.

(56) References Cited

U.S. PATENT DOCUMENTS

| | | | |
|---|---|---|---|
| 6,268,592 B1 * | 7/2001 | Hu | A47J 39/006 |
| | | | 99/378 |
| 2011/0054387 A1 * | 3/2011 | Stern | A61M 39/0208 |
| | | | 604/23 |

* cited by examiner

Primary Examiner — Michael L Hobbs
(74) Attorney, Agent, or Firm — KRIEGSMAN & KRIEGSMAN

(57) ABSTRACT

System for gas treatment of cellular implants. The system enhances the viability and function of cellular implants, particularly those with high cellular density, for use in human or veterinary medicine. The system utilizes a miniaturized electrochemical gas generator subsystem that continuously supplies oxygen and/or hydrogen to cells within an implantable and immunoisolated cell containment subsystem to facilitate cell viability and function at high cellular density while minimizing overall implant size. The cell containment subsystem is equipped with features to allow gas delivery through porous tubing or gas-only permeable internal gas compartments within the implantable cell containment subsystem. Furthermore, the gas generator subsystem includes components that allow access to water for electrolysis while implanted, thereby promoting long-term implantability of the gas generator subsystem. An application of the system is a pancreatic islet (or pancreatic islet analogue) implant for treatment of Type 1 diabetes (T1D) that would be considered a bio-artificial pancreas.

20 Claims, 16 Drawing Sheets

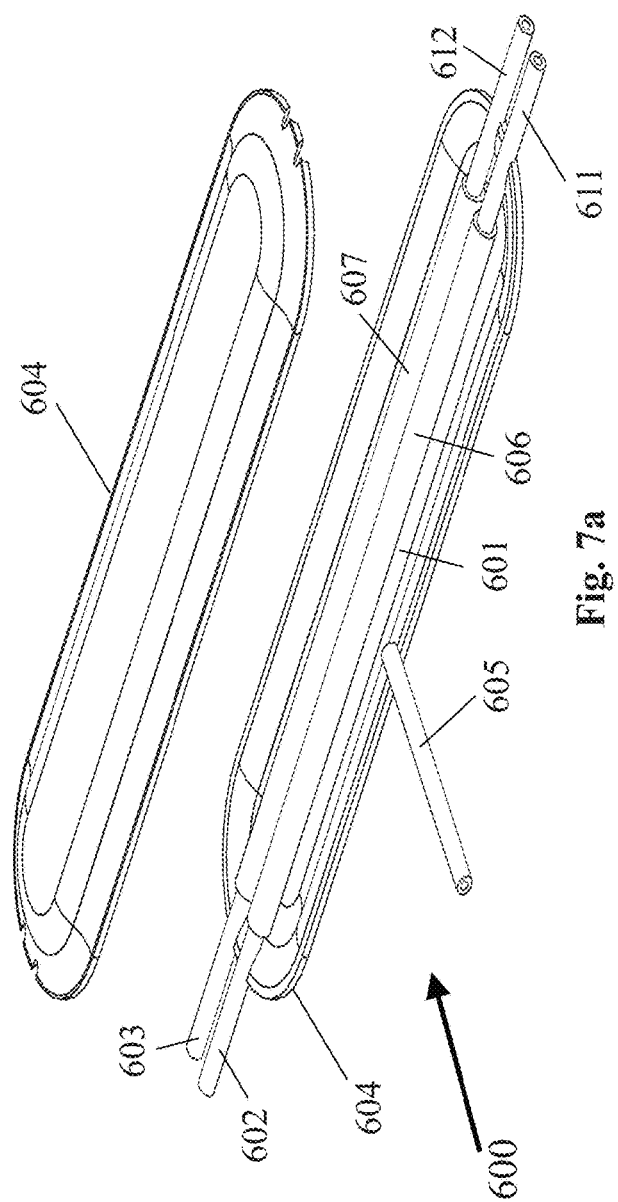
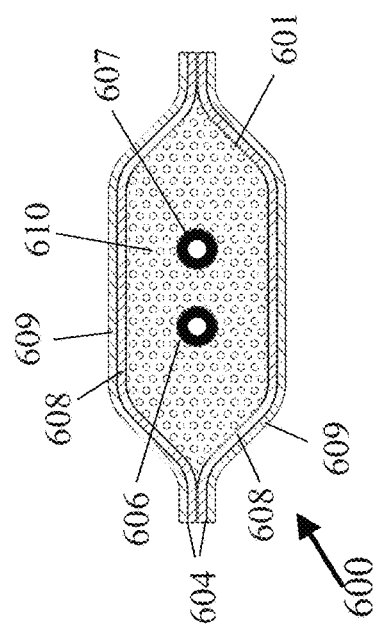
Fig. 7a
Fig. 7b

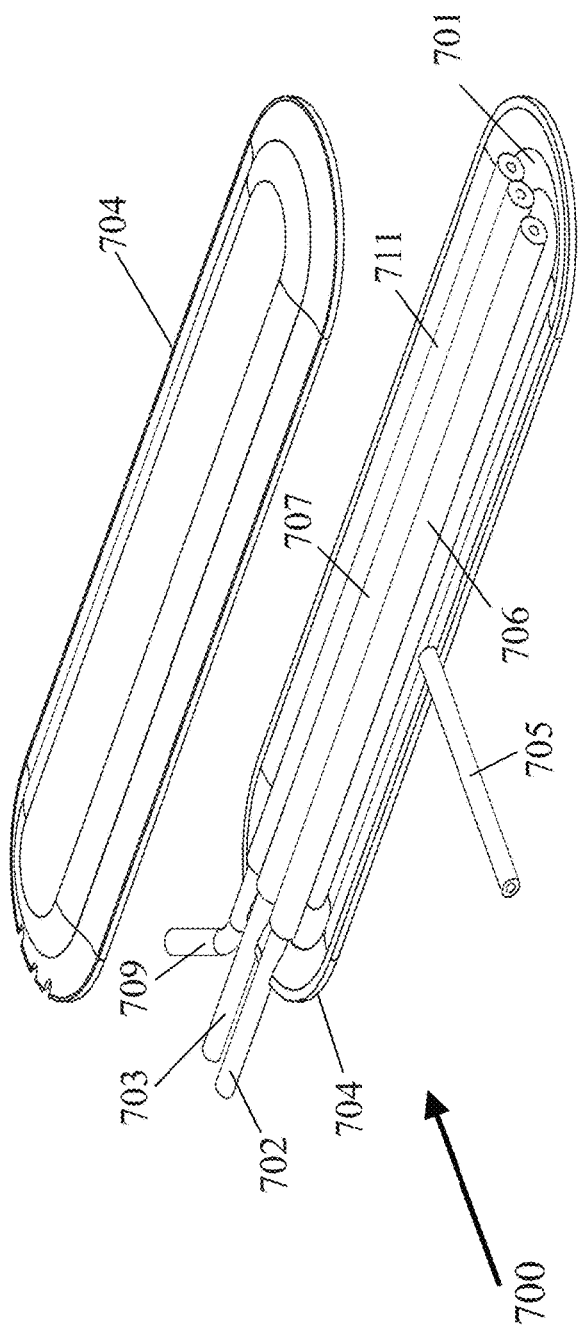
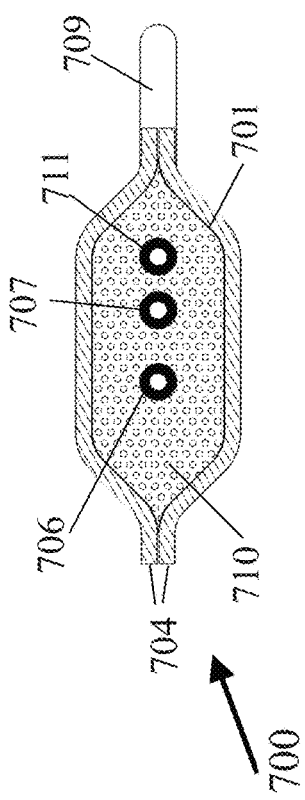
Fig. 8a
Fig. 8b

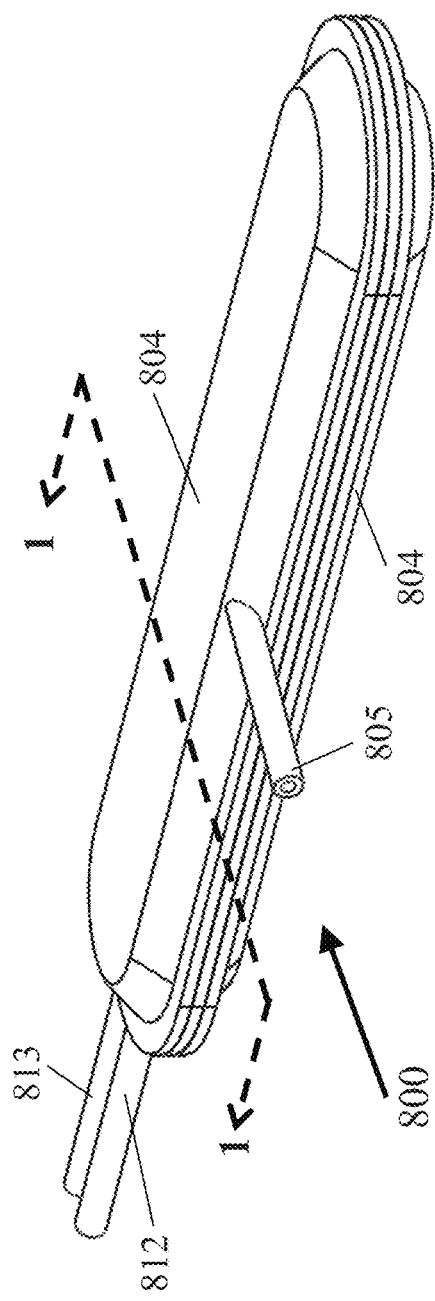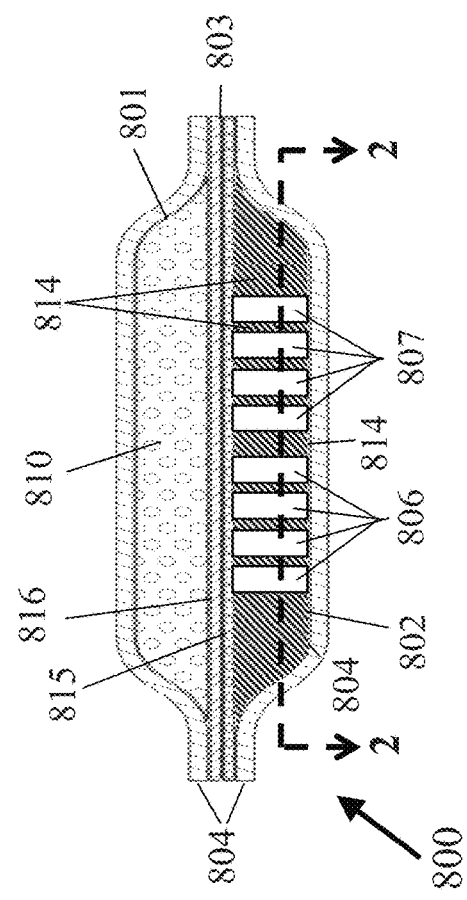

SYSTEM FOR GAS TREATMENT OF A CELL IMPLANT

CROSS-REFERENCE TO RELATED APPLICATIONS

The present application is a continuation of U.S. patent application Ser. No. 16/266,687, filed Feb. 4, 2019, which, in turn, is a continuation of U.S. patent application Ser. No. 14/495,644, filed Sep. 24, 2014, now U.S. Pat. No. 10,231,817, which, in turn, claims the benefit under 35 U.S.C. 119(e) of U.S. Provisional Patent Application No. 61/881,654, filed Sep. 24, 2013, the disclosures of all of which are incorporated herein by reference.

BACKGROUND OF THE INVENTION

The present invention relates generally to implant devices and relates more particularly to a system for gas treatment of a cell implant.

Implant devices are useful for introducing therapeutics in the treatment of diseases, disorders, and/or conditions. Cells and/or tissues are encapsulated within an implant device that allows for dissemination of a therapeutic while limiting an immunological response. Control of delivery of gases and nutrients is important for viability and function of encapsulated cells. A variety of devices and methods have been developed to control delivery of the therapeutics. These devices and techniques typically rely on a large form factor with low cell density for supplying gases and nutrients by diffusion.

SUMMARY OF THE INVENTION

It is an object of the present invention to provide a novel system for gas treatment of a cell implant.

According to one aspect of the invention, there is provided a system for gas treatment of a cell implant, the system comprising (a) a gas generating subsystem, the gas generating subsystem comprising (i) an electrochemical device, the electrochemical device being configured to output a first gas, and (ii) a semipermeable membrane enclosure, the semipermeable membrane enclosure substantially completely encapsulating the electrochemical device, the semipermeable membrane enclosure being constructed to allow for passage therethrough of reactant needed by the electrochemical device; and (b) a cell containment subsystem, the cell containment subsystem comprising a first chamber configured to receive cells, the first chamber receiving the first gas outputted by the electrochemical device.

In another, more detailed feature of the invention, the electrochemical device may comprise an electrolyzer.

In another, more detailed feature of the invention, the electrolyzer may comprise a water electrolyzer.

In another, more detailed feature of the invention, the water electrolyzer may comprise a reservoir for holding a quantity of water.

In another, more detailed feature of the invention, the first gas may comprise gaseous oxygen.

In another, more detailed feature of the invention, the first gas may comprise gaseous hydrogen.

In another, more detailed feature of the invention, the electrochemical device may be further configured to output a second gas.

In another, more detailed feature of the invention, the first chamber may receive the second gas outputted by the electrochemical device.

In another, more detailed feature of the invention, the first gas may comprise gaseous oxygen and the second gas may comprise gaseous hydrogen.

In another, more detailed feature of the invention, the semipermeable membrane enclosure may be further constructed to allow for penetration thereinto of microvasculature of a patient.

In another, more detailed feature of the invention, the semipermeable membrane enclosure may consist of a single layer.

In another, more detailed feature of the invention, the semipermeable membrane enclosure may have a pore size of no greater than about 0.5 μm.

In another, more detailed feature of the invention, the semipermeable membrane enclosure may have a thickness of about 30 μm to about 50 μm.

In another, more detailed feature of the invention, the semipermeable membrane enclosure may comprise a plurality of layers.

In another, more detailed feature of the invention, the semipermeable membrane enclosure may comprise an inner layer and an outer layer, the inner layer may have a pore size of no greater than about 0.5 μm, and the outer layer may have a pore size suitable for the penetration thereinto of microvasculature.

In another, more detailed feature of the invention, the semipermeable membrane enclosure may comprise a top portion and a bottom portion, and the top portion and the bottom portion may be joined together to define a space within which the electrochemical device is disposed.

In another, more detailed feature of the invention, at least a portion of the first chamber may be defined by a wall comprising an immuno-isolation membrane.

In another, more detailed feature of the invention, at least a portion of the first chamber may be defined by a wall comprising a vascularizing membrane.

In another, more detailed feature of the invention, at least a portion of the first chamber may be defined by a multilayer wall comprising an immuno-isolation membrane and a vascularizing membrane.

In another, more detailed feature of the invention, the gas generating subsystem may further comprise a first gas supply tube, the first gas supply tube may have a first end and a second end, and the first end of the first gas supply tube may be fluidly coupled to the electrochemical device to receive the first gas from the electrochemical device.

In another, more detailed feature of the invention, the cell containment subsystem may further comprise a first delivery tube for use in conveying the first gas to cells in the first chamber, the first delivery tube may have a first end, a second end, and a side wall, and the first end of the first delivery tube may be fluidly coupled to the second end of the first gas supply tube.

In another, more detailed feature of the invention, the first delivery tube may be disposed within the first chamber of the cell containment subsystem and may be constructed for the first gas to be delivered to the first chamber through at least one of the second end of the first delivery tube and the side wall of the first delivery tube.

In another, more detailed feature of the invention, the first chamber of the cell containment subsystem may have a selectively permeable wall, the selectively permeable may be permeable to gas but not to cells, and the first delivery tube may be disposed outside the first chamber proximate to the selectively permeable wall of the first chamber.

In another, more detailed feature of the invention, the cell containment subsystem may further comprise a second chamber, the second chamber may be separated from the first chamber by the selectively permeable wall, and the first delivery tube may be formed in the second chamber against the selectively permeable wall as a supply channel.

In another, more detailed feature of the invention, the first delivery tube may be spaced apart from the selectively permeable wall of the first chamber by a distance.

In another, more detailed feature of the invention, the distance by which the first delivery tube may be spaced apart from the selectively permeable wall of the first chamber may be up to 5 mm.

In another, more detailed feature of the invention, the first chamber may comprise a cell supply port.

In another, more detailed feature of the invention, the gas generating subsystem and the cell containment subsystem may be configured for implantation in a patient.

According to another aspect of the invention, there is provided the combination of the above-described system and a quantity of cells disposed in the first chamber of the cell containment subsystem.

According to another aspect of the invention, there is provided a system for gas treatment of a cell implant, the system comprising (a) an electrochemical device, the electrochemical device being configured to output a first gas from a first outlet and a second gas from a second outlet, (b) an implantable cell container, the implantable cell container comprising a first chamber configured to receive cells, (c) a first gas conduit for delivering the first gas from the electrochemical device to the implantable cell container, the first gas conduit comprising a first end and a second end, the first end of the first gas conduit being fluidly coupled to the first outlet of the electrochemical device, the second end of the first gas conduit being configured to deliver the first gas to the first chamber of the implantable cell container, and (d) a second gas conduit for delivering the second gas from the electrochemical device to the implantable cell container, the second gas conduit comprising a first end and a second end, the first end of the second gas conduit being fluidly coupled to the second outlet of the electrochemical device, the second end of the second gas conduit being configured to deliver the second gas to the first chamber of the implantable cell container.

In another, more detailed feature of the invention, at least a portion of the first chamber may be surrounded by an immuno-isolation membrane.

In another, more detailed feature of the invention, each of the second end of the first gas conduit and the second end of the second gas conduit may be disposed within the first chamber.

In another, more detailed feature of the invention, the second end of the first gas conduit may be disposed within the first chamber, and the second end of the second gas conduit may be disposed outside of the first chamber.

In another, more detailed feature of the invention, the first chamber may have a selectively permeable wall, the selectively permeable wall may be permeable to gas but not to cells, and the second end of the second gas conduit may be disposed outside of the implantable cell container in proximity to the selectively permeable wall.

In another, more detailed feature of the invention, the selectively permeable wall may be permeable only to gas.

In another, more detailed feature of the invention, the second end of the second gas conduit may be no more than 5 mm away from the wall of the implantable cell container.

In another, more detailed feature of the invention, the implantable cell container may further comprise a second chamber, the first chamber and the second chamber may be separated by a first selectively permeable wall, the first selectively permeable wall may be permeable to gas but not to cells, and each of the second end of the first gas conduit and the second end of the second gas conduit may be disposed within the second chamber.

In another, more detailed feature of the invention, the implantable cell container may further comprise a third chamber, the third chamber may be configured to receive cells, the second chamber and the third chamber may be separated by a second selectively permeable wall, and the second selectively permeable wall may be permeable to gas but not to cells.

In another, more detailed feature of the invention, each of the first and second selectively permeable walls may be permeable only to gas.

In another, more detailed feature of the invention, the implantable cell container may further comprise a second chamber and a third chamber, the first chamber and the second chamber may be separated by a first selectively permeable wall, the first selectively permeable wall may be permeable to gas but not to cells, the second chamber and the third chamber may be separated by a second selectively permeable wall, the second selectively permeable wall may be permeable to gas but not to cells, the third chamber may be configured to receive cells, and at least one of the second end of the first gas conduit and the second end of the second gas conduit may be positioned within the second chamber.

In another, more detailed feature of the invention, each of the first and second selectively permeable walls may be permeable only to gas.

In another, more detailed feature of the invention, the implantable cell container may further comprise a cell supply port.

In another, more detailed feature of the invention, the electrochemical device may be a water electrolyzer, the first gas may be gaseous oxygen, and the second gas may be gaseous hydrogen.

In another, more detailed feature of the invention, a quantity of cells may be disposed in the first chamber of the implantable cell container.

According to another aspect of the invention, there is provided a system for gas treatment of a cell implant, the system comprising (a) an electrochemical device, the electrochemical device being configured to output a first gas from a first outlet, (b) an implantable cell container, the implantable cell container comprising a first chamber configured to receive cells and a cell supply port through which cells may be supplied to the first chamber, and (c) a first gas conduit for delivering the first gas from the electrochemical device to the implantable cell container, the first gas conduit comprising a first end and a second end, the first end of the first gas conduit being fluidly coupled to the first outlet of the electrochemical device, the second end of the first gas conduit being configured to deliver the first gas to the first chamber of the implantable cell container.

In another, more detailed feature of the invention, at least a portion of the first chamber may be surrounded by an immuno-isolation membrane.

In another, more detailed feature of the invention, the second end of the first gas conduit may be disposed within the first chamber.

In another, more detailed feature of the invention, the second end of the first gas conduit may be disposed outside of the first chamber.

In another, more detailed feature of the invention, the first chamber may have a selectively permeable wall, the selectively permeable wall may be permeable to gas but not to cells, and the second end of the first gas conduit may be disposed outside of the implantable cell container in proximity to the selectively permeable wall.

In another, more detailed feature of the invention, the second end of the first gas conduit may be no more than 5 mm away from the selectively permeable wall of the implantable cell container.

In another, more detailed feature of the invention, the implantable cell container may further comprise a second chamber, the first chamber and the second chamber may be separated by a first selectively permeable membrane, the first selectively permeable membrane may be permeable to gas but not to cells, and the second end of the first gas conduit may be disposed within the second chamber.

In another, more detailed feature of the invention, the implantable cell container may further comprise a third chamber, the third chamber may be configured to receive cells, the second chamber and the third chamber may be separated by a second selectively permeable membrane, and the second selectively permeable membrane may be permeable to gas but not to cells.

In another, more detailed feature of the invention, the electrochemical device may be a water electrolyzer and the first gas may be gaseous oxygen.

In another, more detailed feature of the invention, the electrochemical device may be an electrochemical oxygen concentrator and the first gas may be gaseous oxygen.

According to another aspect of the invention, there is provided the combination of a system as described above and a quantity of cells disposed in the first chamber of the implantable cell container.

According to another aspect of the invention, there is provided a system for gas treatment of a cell implant, the system comprising (a) an electrochemical device, the electrochemical device being configured to output a first gas from a first outlet; (b) an implantable cell container, the implantable cell container comprising a first chamber and a second chamber, the first chamber and the second chamber being separated by a first selectively permeable membrane, the first selectively permeable membrane being permeable to gas but not to cells, the first chamber being configured to receive cells, the second chamber comprising a supply channel in communication with the first selectively permeable membrane; (c) a first gas conduit for delivering the first gas from the electrochemical device to the implantable cell container, the first gas conduit comprising a first end and a second end, the first end of the first gas conduit being fluidly coupled to the first outlet of the electrochemical device, the second end of the first gas conduit being coupled to an end of the supply channel.

In another, more detailed feature of the invention, the first chamber may include a cell supply port through which cells may be supplied to the first chamber.

In another, more detailed feature of the invention, at least a portion of the first chamber may be surrounded by an immuno-isolation membrane.

In another, more detailed feature of the invention, the implantable cell container may further comprise a third chamber, the second chamber and the third chamber may be separated by a second selectively permeable membrane, the second selectively permeable membrane may be permeable to gas but not to cells, the third chamber may be configured to receive cells, and the supply channel may be in communication with the second selectively permeable membrane.

In another, more detailed feature of the invention, the electrochemical device may be a water electrolyzer and the first gas may be gaseous oxygen.

In another, more detailed feature of the invention, the electrochemical device may be an electrochemical oxygen concentrator and the first gas may be gaseous oxygen.

In another, more detailed feature of the invention, the first selectively permeable membrane may be permeable only to gas.

According to another aspect of the invention, there is provided the combination of the system as described above and a quantity of cells disposed in the first chamber of the implantable cell container.

According to another aspect of the invention, there is provided a cell container comprising (a) a first chamber, the first chamber being configured to receive cells and being bounded in part by a first selectively permeable membrane, the first selectively permeable membrane being permeable only to gas; and (b) a second chamber, the second chamber being bounded in part by the first selectively permeable membrane, the second chamber comprising a first gas supply channel in communication with the first selectively permeable membrane.

In another, more detailed feature of the invention, the first chamber may comprise a cell supply port through which cells may be supplied to the first chamber.

In another, more detailed feature of the invention, at least a portion of the first chamber may be surrounded by an immuno-isolation membrane.

In another, more detailed feature of the invention, the implantable cell container may further comprise a third chamber, the second chamber and the third chamber may be separated by a second selectively permeable membrane, the second selectively permeable membrane may be permeable only to gas, the third chamber may be configured to receive cells, and the first gas supply channel may be in communication with the second selectively permeable membrane.

In another, more detailed feature of the invention, the second chamber may further comprise a second gas supply channel, and the second gas supply channel may be in communication with each of the first selectively permeable membrane and the second selectively permeable membrane.

In another, more detailed feature of the invention, the second chamber may further comprise a second gas supply channel, and the second gas supply channel may be in communication with the first selectively permeable membrane.

According to another aspect of the invention, there is provided a system for the gas treatment of cell implants, comprising (a) an electrochemical gas generating subsystem; (b) a cell containment subsystem comprising a sealed volume to be filled with cells and configured to receive gas outputs from the electrochemical gas generating subsystem; and (c) impermeable tubing connected from the electrochemical gas generating subsystem outlets to the cell containment subsystem inlets, wherein the gases flowing from the outlets of the electrochemical gas generating subsystem to the inlets cell containment subsystem inlets, then to the inner volume, continue to diffuse outward from within the inner volume so that when the implant has a cell packing density of 6,600-8,000 islet equivalents per exposed surface area in $cm^2$ of the cell container and an overall dose of up to 100 IEQ/g rodent body weight in the cell container the rodent recipient has a measured daily blood glucose level of 50-200 mg/dL in the absence of insulin treatment over a at least a 14 day period.

According to another aspect of the invention, there is provided a system for gas treatment of a cell implant, the system comprising (a) a gas generating subsystem, the gas generating subsystem comprising (i) an electrochemical device, the electrochemical device being configured to output a first gas, the first gas comprising gaseous oxygen, the electrochemical device comprising a reservoir, and (ii) a quantity of $H_2O^{17}$ disposed within the reservoir, whereby the first gas outputted by the electrochemical comprises $O_2^{17}$; and (b) a cell containment subsystem, the cell containment subsystem comprising a first chamber configured to receive cells, the first chamber receiving the first gas comprising $O_2^{17}$ outputted by the electrochemical device.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIG. 7*a* is partly exploded perspective view of one embodiment of a cell containment system that may be used in the system of FIG. 1;

FIG. 7*b* is a transverse section view of the cell containment system of FIG. 7*a*;

FIG. 8*a* is partly exploded perspective view of another embodiment of a cell containment system that may be used in the system of FIG. 1;

FIG. 8*b* is a transverse section view of the cell containment system of FIG. 8*a*;

FIG. 9*a* is a perspective view of another embodiment of a cell containment system that may be used in the system of FIG. 1;

FIG. 9*b* is a section view of the cell containment system of FIG. 9*a* taken along line 1-1;

DETAILED DESCRIPTION OF THE INVENTION

Figure 1:
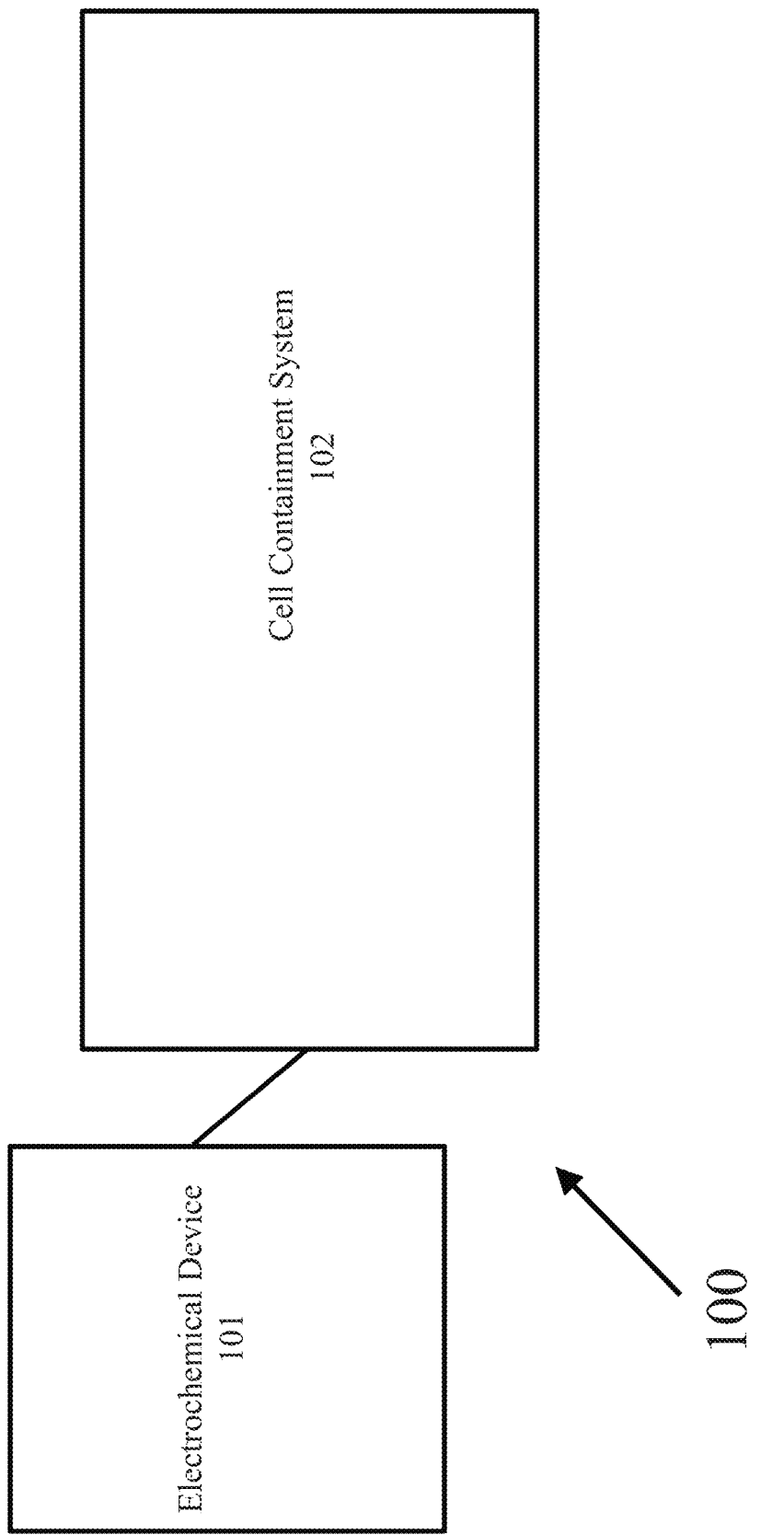
FIG. 1 is a block diagram of one embodiment of a system for the gas treatment of a cell implant according to the teachings of the present invention.

The present invention is directed at a system for the gas treatment of cell implants that supplies gases, nutrients, and other active compounds to cells. The system for the gas treatment of cell implants may comprise an electrochemical device and a cell containment system wherein impermeable tubing connects the outlets of the electrochemical device to the inlets of the cell containment system.

In one embodiment wherein the electrochemical device is an electrolyzer, the system for the gas treatment of cell implants may comprise an electrochemical device located above or below the surface of the skin, a cell containment system located below the surface of the skin, and impermeable tubing connecting the outlets said electrochemical device to the inlets of said cell containment system. The cell containment system may be located subcutaneously, intraperitoneally, or in a cerebral spinal fluid space. Specific subcutaneously locations may include, but are not limited to, areas overlapping muscle tissues for enhanced vascularization.

In another embodiment wherein the electrochemical device is an electrolyzer, the system for the gas treatment of cell implants may comprise an electrochemical device and cell containment system that are integrated into a single unit with internal impermeable tubing connecting the outlets of said electrolyzer to the inlets of said cell containment system. The system for the gas treatment of cell implants may be located subcutaneously, intraperitoneally, or in a cerebral spinal fluid space. Specific subcutaneously locations may include, but are not limited to, areas overlapping muscle tissues for enhanced vascularization.

In one embodiment wherein the electrochemical device is an electrochemical oxygen concentrator, the system for the gas treatment of cell implants may comprise an electrochemical device located above surface of the skin, a cell containment system located above or below the surface of the skin, and impermeable tubing connecting the outlet of said electrochemical oxygen concentrator to the inlet of said cell containment system.

In one embodiment, the electrochemical device may comprise an electrolyzer device wherein the electrolyzer electrolyzes water vapor obtained from the body (e.g. interstitial fluid, blood) or ambient air, and delivers the outputted oxygen and/or hydrogen gas to the cell containment system.

In another embodiment, the electrolyzer device further comprises a membrane enclosure that substantially encapsulates the electrolyzer device housing, and partially encapsulates the $O_2$ and $H_2$ supply tubes connected to the gas outlets of the electrolyzer device. The membrane enclosure may comprise a composite of two membranes. The composite inner membrane (i.e. the membrane closest to the electrolyzer device housing) may comprise a selectively membrane that prevents bio-fouling, does not let cells pass through said composite inner membrane, but allows liquids and gases to pass through said composite inner membrane. Examples of the composite inner membrane include, but are not limited to, expanded PTFE with a pore size of 0.5 μm or less, silicone rubber, and TEFLON® polytetrafluoroethylene. The preferred thickness of the composite inner membrane is 30-50 μm. The composite outer membrane may comprise a vascularizing membrane that allows for the growth and presence of the microvasculature within said composite outer membrane, but the microvasculature does not penetrate composite inner membrane 304. An example of this outer membrane is expanded PTFE with at least some of the pores being 3 μm or greater in diameter. The preferred thickness range of the composite outer membrane is 30-50 μm. The composite inner membrane and the composite outer membrane may be secured together using hot-pressing or ultrasonic welding. In an alternative embodiment, the membrane enclosure may comprise a single membrane. The single membrane may comprise a vascularizing membrane that allows for the growth and presence of the microvasculature within said single membrane. An example of this single membrane is expanded PTFE with at least some of the pores being 3 μm or greater in diameter. The preferred thickness range of this single membrane is 30-50 μm.

In another embodiment, the electrochemical device may further comprise an electrolyzer device with a refillable water reservoir that delivers oxygen and/or hydrogen from the outlets of the electrolyzer device to the inlets of the cell containment system. In a further embodiment, the water reservoir may be filled with $H_2O^{17}$ wherein the electrolysis of $H_2O^{17}$ produces $O_2^{17}$, which is delivered to the cell containment system. The water reservoir may be refilled via a sealable tubing located above or below the surface of the skin.

In another embodiment, the electrolyzer device may further comprise control electronics and an energy supply. The energy supply may comprise a rechargeable or non-rechargeable coin battery that is replaceable and located inside the electrolyzer housing. In an alternative embodiment, the energy supply may comprise a larger energy compartment outside the body that may supply energy to a rechargeable battery located inside the electrolyzer housing. The larger energy compartment outside the body may comprise a rechargeable or non-rechargeable battery (e.g. alkaline battery) located in a housing or battery pack that transfer energy to the rechargeable battery internal to the electrolyzer device via electrical wiring. In another alternative embodiment, the energy compartment may be located outside of the body and may use rechargeable or non-rechargeable batteries (e.g. alkaline batteries) to transfer energy via electrical wiring to positive and negative terminals in the electrolyzer device (i.e. there is no internal battery in the electrolyzer device). In another embodiment, the energy supply may comprise a system for transcutaneous energy transfer wherein an external power source (e.g. rechargeable or non-rechargeable battery) coupled to a magnetic coil located outside the body transfers charge to a magnetic coil and/or battery internally located within the electrolyzer device.

In another embodiment, the electrochemical device may comprise an electrochemical oxygen concentrator (EOC) device that is located above the surface of the skin, and delivers oxygen from the outlet of the EOC to the inlet of the cell containment system. In another embodiment, the electrochemical oxygen concentrator device may further comprise control electronics and an energy supply. The energy supply may comprise a rechargeable or non-rechargeable coin battery that is replaceable and located inside the EOC housing. In an alternative embodiment, the energy supply may comprise a larger energy compartment outside the body that may supply energy to a rechargeable battery located inside the EOC housing. The larger energy compartment outside the body may comprise a rechargeable or non-rechargeable battery (e.g. alkaline battery) located in a housing or battery pack that transfer energy to the rechargeable battery internal to the EOC device via electrical wiring. In yet another embodiment, the energy supply may comprise a system for transcutaneous energy transfer wherein an external power source (e.g. rechargeable or non-rechargeable battery) coupled to a magnetic coil located outside the body transfers charge to a magnetic coil and/or battery internally located within the EOC device.

In one embodiment, the cell containment system may comprise a single internal compartment wherein internal permeable tubing delivers hydrogen and oxygen gas to the surrounding cells. For efficient gas distribution to cells, the dimensions of the internal compartment are preferably 20 cm or less in length, 20 cm or less in width, and 3 mm or less in height. The internal compartment may be filled with cells using a sealable, impermeable cell supply tube secured within the exterior walls with access to the first internal cell compartment. The internal compartment is bound by the exterior walls of the cell containment device. The exterior walls of the cell containment device may comprise a composite of a selectively permeable membrane and a vascularizing membrane, said selectively permeable membrane and said vascularizing membrane secured together using ultrasonic welding or hot-pressing. The selectively permeable membrane may comprise a membrane that prevents bio-fouling, does not let cells pass through said selectively permeable membrane, but allows liquids and gases to pass through said selectively permeable membrane. An example of the selectively permeable membrane includes, but is not limited to, expanded PTFE with a pore size of 0.5 μm or less. The preferred thickness of the selectively permeable membrane is 30-50 μm. The vascularizing membrane may comprise a membrane that allows for the growth and presence of the microvasculature within said vascularizing membrane, but the microvasculature does not penetrate the selectively permeable membrane. An example of this vascularizing membrane is expanded PTFE with at least some of the pores being 3 μm or greater in diameter. The preferred thickness range of the vascularizing membrane is 30-50 μm. In an alternative embodiment, the exterior walls may comprise a single vascularizing membrane that allows the microvasculature to penetrate into the interior compartment, but does not allow the interior cells, particularly cell clusters (e.g. islets) pass through the membrane. An example of this single membrane is expanded PTFE with at least some of the pores being 3 μm or greater in diameter. The preferred thickness range of this single membrane is 30-50 μm. The internal tubing in contact with the cells may comprise permeable tubing (e.g. NAFION® perfluorinated ion-exchange membrane, GORE-TEX® expanded polytetrafluoroethylene, and silicone rubber), said permeable tubing secured to impermeable tubing (e.g. TEFLON® polytetrafluoroethylene, polypropylene, polycarbonate, and tygon) from the outlet of the electrochemical device, that allows oxygen and/or hydrogen gas to diffuse out of said internal permeable tubing into the surrounding cells. The internal tubing may further comprise open-ended permeable tubing that allows oxygen and/or hydrogen gas to diffuse out the open end of the tubing and into the surrounding cells.

In another embodiment, the cell containment system may further comprise venting tubes to prevent excess gas build-up in the internal permeable tubing. The venting tubes may comprise impermeable tubing secured to the ends of the internal permeable tubing, and the other end located external to the cell containment system and above the surface of the skin.

In another embodiment, the cell containment system may further comprise a third permeable nutrient delivery tube for transferring active compounds (e.g. $N_2$, $CO_2$, NO, nutrients, growth factors, and hormones) into the cell compartment from an external source. A sealable, impermeable nutrient supply tube will have one end located above or below the surface of the skin that will provide access for inputting nutrients from an external source. The other end of the impermeable nutrient supply tube will be secured to the internal permeable nutrient delivery tube internal to the cell containment system. Nutrients may diffuse into the cells surrounding the permeable nutrient delivery tube through the wall of the permeable nutrient delivery tube or out of the open end of the permeable nutrient delivery tube.

In one embodiment, the cell containment system may comprise two internal compartments. The first internal cell compartment may comprise a volume to be filled with cells using a sealable, impermeable cell supply tube secured within the exterior walls and with access to the first internal cell compartment. The second internal gas compartment may comprise a volume that receives oxygen and/or hydrogen gas flowing from the electrochemical device. For efficient gas distribution to cells, the dimensions of first internal cell compartment are preferably 20 cm or less in length, 20 cm or less in width, and 1 mm or less in height. The dimensions of internal gas compartment are preferably 20 cm or less in length, 20 cm or less in width, and 3 mm or less in height. The first internal cell compartment may be separated from the second internal gas compartment using a selectively permeable membrane. The selectively permeable membrane may comprise a composite of support membrane and cell isolation membrane. The support membrane may comprise a permeable membrane that also provides rigidity to the cell isolation membrane. Examples of the support membrane include, but are not limited to, expanded PTFE with a pore size of 3 µm or greater, silicone rubber, TEFLON® polytetrafluoroethylene, and GORE-TEX® expanded polytetrafluoroethylene. The preferred thickness range of the support membrane is 30-50 µm. The cell isolation membrane may comprise a gas-only permeable membrane that prevents cells and liquids in the first internal cell compartment from passing into the second internal gas compartment. Examples of the cell isolation membrane include, but are not limited to, expanded PTFE with a pore size of 0.5 µm or less, silicone rubber, TEFLON® polytetrafluoroethylene, and GORE-TEX® expanded polytetrafluoroethylene. The preferred thickness range of the cell isolation membrane is 30-50 µm. The support membrane and the cell isolation membrane may be bonded together using hot-pressing or ultrasonic welding. In an alternative embodiment, the selectively permeable membrane may comprise a single permeable membrane that allows gas and liquids to pass through the membrane, but prevents cells in the first internal cell compartment from passing into the second internal gas compartment. An example of this single membrane includes, but is not limited to, expanded PTFE with a pore size of 1.0 µm or greater. The preferred thickness range of this single membrane is 30-50 µm. The second internal gas compartment may further comprise two sets of isolated channels wherein one set of isolated channels is supplied with oxygen via impermeable tubing connected to the anode outlet of the electrolyzer device, and one set of channels is supplied with hydrogen via impermeable tubing connected to the cathode outlet of the electrolyzer device. At least one gas-impermeable wall will separate the two sets of isolated channels to prevent oxygen and hydrogen gas from combining in the second internal gas compartment. The gas impermeable walls may comprise a gas impermeable polymer or plastic.

In another embodiment, the cell containment system may comprise three internal compartments. The center internal gas compartment may comprise a volume that receives oxygen and/or hydrogen gas flowing from the electrochemical device. The two compartments on each side of the center internal gas compartment may comprise two volumes to be filled with cells using sealable, impermeable cell supply tubes secured within the exterior walls and with access to the two internal cell compartments. For efficient gas distribution to cells, the dimensions of two internal cell compartments are preferably 20 cm or less in length, 20 cm or less in width, and 1 mm or less in height. The dimensions of center internal gas compartment are preferably 20 cm or less in length, 20 cm or less in width, and 3 mm or less in height. The center internal gas compartment may be separated from each of the internal cell compartments on each side using a selectively permeable membrane. The selectively permeable membrane may comprise a composite of support membrane and cell isolation membrane. The support membrane may comprise a permeable membrane that also provides rigidity to the cell isolation membrane. Examples of the support membrane include, but are not limited to, expanded PTFE with a pore size of 3 µm or greater, silicone rubber, TEFLON® polytetrafluoroethylene, and GORE-TEX® expanded polytetrafluoroethylene. The preferred thickness range of the support membrane is 30-50 µm. The cell isolation membrane may comprise a gas-only permeable membrane that prevents cells and liquids in the first internal cell compartment from passing into the second internal gas compartment. Examples of the cell isolation membrane include, but are not limited to, expanded PTFE with a pore size of 0.5 µm or less, silicone rubber, TEFLON® polytetrafluoroethylene, and GORE-TEX® expanded polytetrafluoroethylene. The preferred thickness range of the cell isolation membrane is 30-50 µm. The support membrane and cell isolation membrane may be bonded together using hot-pressing or ultrasonic welding. In an alternative embodiment, the selectively permeable membrane may comprise a single permeable membrane that allows gas and liquids to pass through the membrane, but prevents cells in the first internal cell compartment from passing into the second internal gas compartment. An example of this single membrane includes, but is not limited to, expanded PTFE with a pore size of 1.0 µm or greater. The preferred thickness range of this single membrane is 30-50 µm. The center internal gas compartment may further comprise two sets of isolated channels wherein one set of isolated channels is supplied with oxygen via impermeable tubing connected to the anode outlet of the electrolyzer device, and one set of channels is supplied with hydrogen via impermeable tubing connected to the cathode outlet of the electrolyzer device. At least one gas-impermeable wall will separate the two sets of isolated channels to prevent oxygen and hydrogen gas from combining in the second internal gas compartment. The cell containment system may further comprise an internal gas permeable membrane that separates the two compartments wherein said internal gas permeable membrane allows oxygen and hydrogen gas to diffuse from the second internal compartment into the first internal compartment containing cells, but the gas permeable membrane prevents cells or liquid from diffusing from the first internal compartment into the second internal compartment. Examples of this internal gas permeable membrane include, but are not limited to, silicone rubber and expanded PTFE with a pore size of 0.5 µm or less. The center internal gas compartment may further comprise two sets of isolated channels wherein one set of isolated channels is supplied with oxygen via impermeable tubing connected to the anode outlet of the electrolyzer device, and one set of channels is supplied with hydrogen via impermeable tubing connected to the cathode outlet of the electrolyzer device. At least one gas-impermeable wall will separate the two sets of isolated channels to prevent oxygen and hydrogen gas from combining in the center internal gas compartment. The gas impermeable walls may comprise a gas impermeable polymer or plastic.

In another embodiment, the cell containment system may comprise three interior compartments for delivering oxygen gas to the interior of the cell containment system, and a hydrogen gas delivery system for delivering hydrogen gas to the exterior of the cell containment system. The hydrogen gas delivery system may comprise one or more open-ended gas permeable tubes located 0-5 mm from the exterior wall(s) of the cell containment system. The open-ended gas permeable tubes may be connected to a hydrogen supply manifold that is supplied with hydrogen gas from the cathode port of the electrolyzer device. The three internal compartments may comprise a center internal gas compartment, and two internal cell compartments on each side of the center internal gas compartment. The center internal compartment may comprise a volume that receives oxygen gas via impermeable tubing connected to the anode port of the electrochemical device. The two cells compartments on each side of the center internal gas compartment may comprise two volumes to be filled with cells using sealable, impermeable cell supply tubes secured within the exterior walls and with access to the two internal cell compartments. The center internal gas compartment may be separated from each of the internal cell compartments on each side using a selectively permeable membrane. The selectively permeable membrane may comprise a composite of support membrane and cell isolation membrane. The support membrane may comprise a permeable membrane that also provides rigidity to the cell isolation membrane. Examples of the support membrane include, but are not limited to, expanded PTFE with a pore size of 3 µm or greater, silicone rubber, TEFLON® polytetrafluoroethylene, and GORE-TEX® expanded polytetrafluoroethylene. The preferred thickness range of the support membrane is 30-50 µm. The cell isolation membrane may comprise a gas-only permeable membrane that prevents cells and liquids in the first internal cell compartment from passing into the second internal gas compartment. Examples of the cell isolation membrane include, but are not limited to, expanded PTFE with a pore size of 0.5 µm or less, silicone rubber, TEFLON® polytetrafluoroethylene, and GORE-TEX® expanded polytetrafluoroethylene. The preferred thickness range of the cell isolation membrane is 30-50 µm. The support membrane and the cell isolation membrane may be bonded together using hot-pressing or ultrasonic welding. In an alternative embodiment, the selectively permeable membrane may comprise a single permeable membrane that allows gas and liquids to pass through the membrane, but prevents cells in the first internal cell compartment from passing into the second internal gas compartment. An example of this single membrane includes, but is not limited to, expanded PTFE with a pore size of 1.0 µm or greater. The preferred thickness range of this single membrane is 30-50 µm.

Referring now to FIG. 1, there is shown one embodiment of a system for the gas treatment of cell implants according to the present invention, the system being represented generally by reference numeral 100.

System 100 may comprise an electrochemical device 101 and a cell containment system 102, electrochemical device 101 delivering oxygen and/or hydrogen to cell containment system 102.

In one embodiment, electrochemical device 101 may be an electrolyzer, and system 100 may comprise electrochemical device 101 being located above or below the surface of the skin, cell containment system 102 being located below the surface of the skin, and impermeable tubing connecting said electrolyzer to said cell containment system. Cell containment system 102 may be located, for example, subcutaneously, intraperitoneally, or in a cerebral spinal fluid space. Specific subcutaneously locations may include, but are not limited to, an area overlapping muscle tissues for enhanced vascularization.

In another embodiment, electrochemical device 101 may be an electrolyzer, and system 100 may comprise electrochemical device 101 and cell containment system 102 integrated into a single unit with internal impermeable tubing connecting said electrolyzer to said cell containment system. The single unit may be located, for example, subcutaneously, intraperitoneally, or in a cerebral spinal fluid space. Specific subcutaneously locations may include, but are not limited to, an area overlapping muscle tissues for enhanced vascularization.

In another embodiment, electrochemical device 101 may be an electrochemical oxygen concentrator (EOC), and system 100 may comprise an electrochemical device 101 located above surface of the skin, cell containment system 102 located below the surface of the skin, and impermeable tubing connecting said electrochemical oxygen concentrator to said cell containment system.

Figure 2:
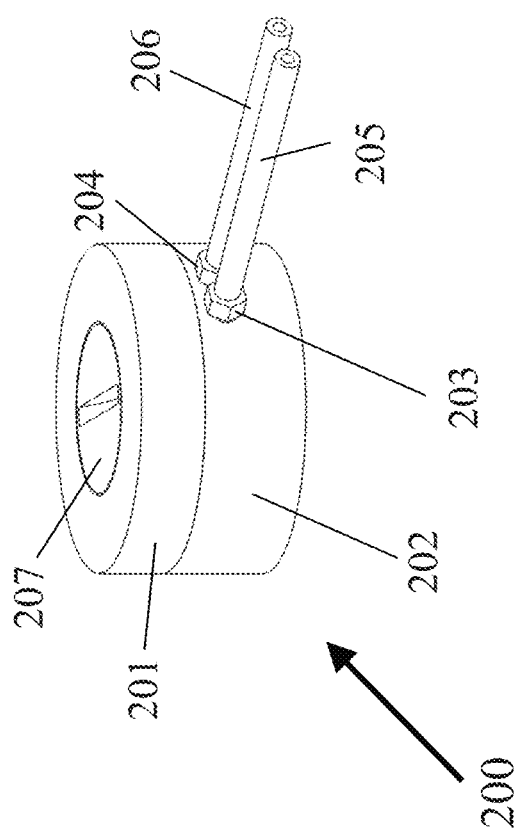
FIG. 2 is a perspective view of one embodiment of an electrolyzer device that may be used in the system of FIG. 1 as the electrochemical device.

An embodiment of the electrochemical device according to the invention is electrolyzer 200, which is shown in FIG. 2. The electrolyzer components are contained within an electrolyzer housing top 201 and an electrolyzer housing bottom 202 wherein the two housing sections are secured together mechanically (e.g. using screws, ultrasonic welding, press-fit housings). Electrolyzer housing top 201 may further comprise a battery lid 207 wherein battery lid 207 may be unscrewed in order to access the rechargeable or non-rechargeable battery contained within the electrolyzer housing top. Electrolyzer 200 may supply oxygen to the cell containment system using an oxygen supply tube 205, which is connected to the anode port via a fitting 203. Electrolyzer 200 may also supply hydrogen to the cell containment system using a hydrogen supply tube 206, which is connected to the cathode port via a fitting 204. The supply tubes may comprise gas impermeable tubing, including, but not limited to, polypropylene, TEFLON® polytetrafluoroethylene, polycarbonate, PVC, and tygon. The anode and cathode port fittings may comprise standard tube fittings, including, but are not limited to, barbed, SWAGELOK® compression fittings, and Luer lock fittings.

Figure 3B:
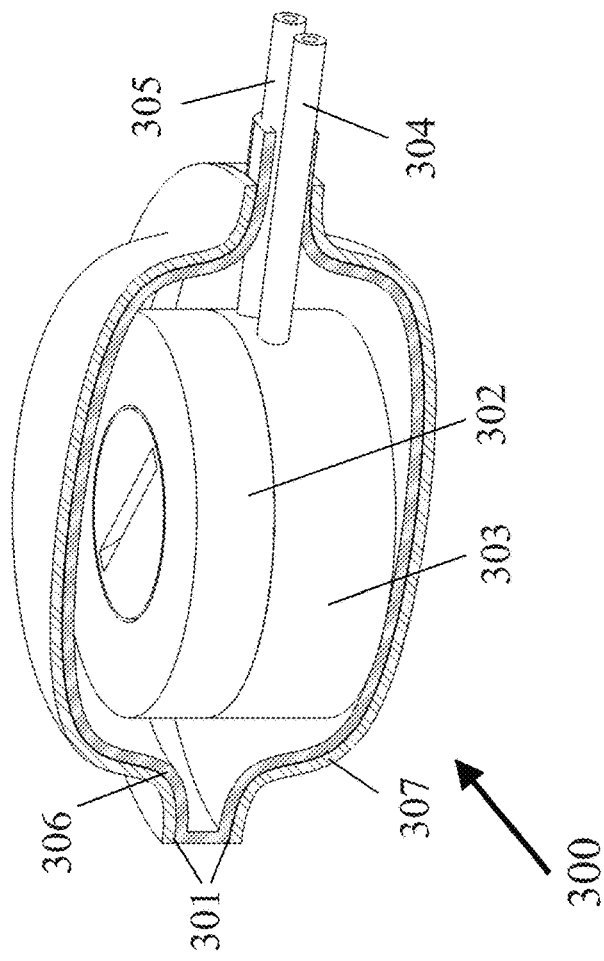
FIG. 3*b* is a perspective view, partly in section, of the electrolyzer device shown in FIG. 3*a*.
Figure 3A:
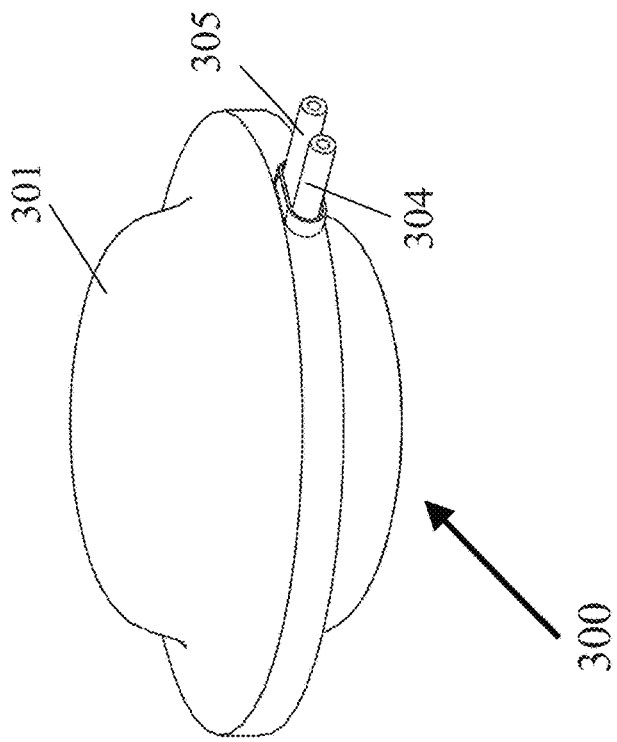
FIG. 3*a* is a perspective view of another embodiment of an electrolyzer device that may be used in the system of FIG. 1 as the electrochemical device.

In another embodiment, which is shown in FIGS. 3a and 3b, the electrochemical device of system 100 may take the form of electrolyzer device 300. Electrolyzer device 300 may further comprise a membrane enclosure 301 that substantially encapsulates an electrolyzer housing top 302 and an electrolyzer housing bottom 303, and partially encapsulates an oxygen supply tube 304 and a hydrogen supply tube 305. Membrane enclosure 301 may comprise a composite of two membranes. An inner membrane 306 of membrane enclosure 301 may comprise a selectively permeable membrane that does not let cells pass through said composite inner membrane, but allows liquids and gases to pass through said composite inner membrane. Examples of the composite inner membrane include, but are not limited to, expanded PTFE with a pore size of 0.5 µm or less, silicone rubber, and TEFLON® polytetrafluoroethylene. The preferred thickness of the composite inner membrane is 30-50 µm. An outer membrane 307 of membrane enclosure 301 may comprise a vascularizing membrane that allows for the growth and presence of the microvasculature within said composite outer membrane, but the microvasculature does not penetrate inner membrane 306. An example of this outer membrane is expanded PTFE with at least some of the pores being 3 µm or greater in diameter. The preferred thickness range of the composite outer membrane is 30-50 µm. Inner membrane 306 and outer membrane 307 may be secured together using hot-pressing or ultrasonic welding. In an alternative embodiment (not shown), membrane enclosure 301 may comprise a single membrane. The single membrane may comprise a vascularizing membrane that allows for the growth and presence of the microvasculature within said single membrane. An example of this single membrane is expanded PTFE with at least some of the pores being 3 µm or greater in diameter. The preferred thickness range of this single membrane is 30-50 µm.

Figure 4:
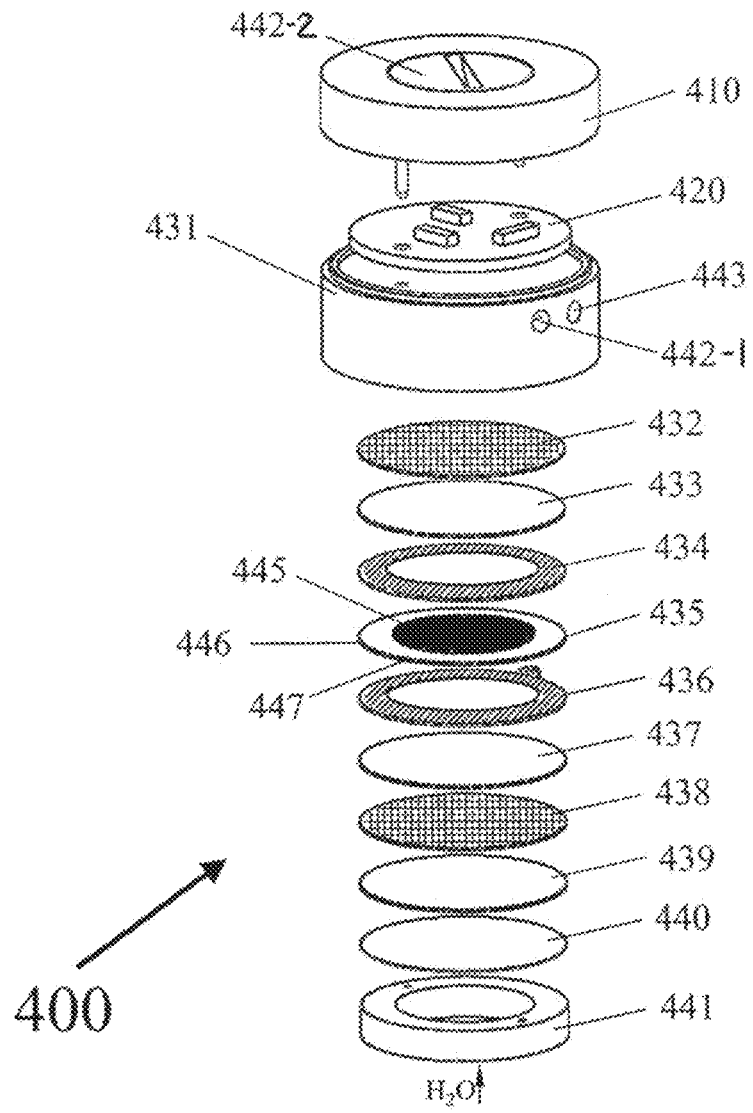
FIG. 4 is an exploded perspective view of another embodiment of an electrolyzer device that may be used in the system of FIG. 1 as the electrochemical device.

An exploded view of another embodiment of an electrolyzer device that may be used as the electrochemical device of system 100 is shown in FIG. 4 and is represented generally by reference numeral 400. Electrolyzer device 400 is a proton-exchange membrane (PEM) based system that performs electrolysis of water. Water enters the cathode side of electrolyzer device 400 via the hole in a retaining ring 441. The source of water vapor may be the body (e.g. intersitital fluid, blood) or ambient air. When electrolyzer device 400 is implanted in the body, a bio-compatible membrane 440 prevents bio-fouling in order to promote a stable and consistent water vapor source. An example of this membrane is expanded PTFE with at least some of the pores being 3 µm or greater in diameter and a preferred thickness range of 30-50 µm. A vapor transport membrane 439 prevents any of the microvasculature penetrating bio-compatible membrane 440 from further penetrating into electrolyzer device 400, while simultaneously preventing bio-fouling and only allowing gases to pass through said vapor transport membrane. Examples of this vapor transport membrane include, but are not limited to, ZITEX" porous polytetrafluoroethylene, GORE-TEX® expanded polytetrafluoroethylene, silicone rubber, PTFE, and TEFLON® polytetrafluoroethylene.

Water vapor diffusing through the cathode side is electrolyzed by a membrane electrode assembly (MEA) 435. MEA 435 may comprise a proton-exchange membrane (PEM) 446 (e.g. NAFION® perfluorinated ion-exchange membrane, SOLVAY® proton-exchange membrane, AQUIVION® perfluorosulfonic acid ionomer membrane) with a cathode 447 (e.g. platinum-black, platinum on carbon, iridium, iridium oxide, ruthenium oxide) adhered to the bottom of PEM 446, and an anode 445 (e.g. platinum-black, platinum on carbon, iridium, iridium oxide, ruthenium oxide) adhered to the top of PEM 435. During the electrolysis of water, $O_2$ and $H^+$ ions are generated at the anode during the anode half-reaction (i.e. $2H_2O \rightarrow O_2 + 4H^+ + 4e^-$). The potential difference between the two electrodes (generated by electronics board 420) drives $H^+$ ions from the anode to the cathode wherein the $H^+$ ions combine with electrons passing through the potentiostatic circuit (on electronics board 420) to form $H_2$ at the cathode during the cathode half-reaction (i.e. $4H^+ + 4e^- \rightarrow 2H_2$). During the electrolysis of $H_2O^{17}$, the anode and cathode undergo the same half-reactions, except that $O_2^{17}$ is primarily produced at the anode instead of $O_2$. Some $O_2$ may be produced at the anode during the electrolysis of $H_2O^{17}$ due to ambient water vapor seeping into the electrolyzer, or any contamination of the $H_2O^{17}$ with $H_2O$.

Vapor transport membranes 433 and 437 provide gas access to MEA 435, but also act as barriers to prevent contaminant liquids from reaching MEA 435. Vapor transport membranes 433 and 437 may comprise membranes identical or similar to vapor transport membrane 439. Current collectors 434 (i.e. positive terminal) and 436 (i.e. negative terminal) provide electrical connections to the potentiostatic circuit on electronics board 420. Current collectors 434 and 436 may comprise a conductive, corrosion-resistant metal, including, but not limited to, a metal from the valve metal group (Ti, Nb, Zr, Ta) or a metal from the noble metal group (Pt, Au, Pd). Support meshes 432 and 438 provide rigidity to the component stack-up and act to evenly distribute the load over the entire MEA surface area. Support meshes 432 and 438 may also comprise a conductive, corrosion-resistant metal, including, but not limited to, a metal from the valve metal group (Ti, Nb, Zr, Ta) or a metal from the noble metal group (Pt, Au, Pd).

$O_2$ and $H_2$ gas generated by the electrolyzer device 400 flow out of an anode port 442-1 and a cathode port 443, respectively, in a housing bottom 431. The preferred range of oxygen concentrations supplied by electrolyzer device 400 (out of anode port 442-1) is 90-100% oxygen gas. The preferred range of pressures for oxygen gas being supplied is 0-100 mmHg above ambient pressure. The preferred range of oxygen flow rates being supplied to the cell containment system is one-tenth the oxygen consumed by the cells in the cell containment system (i.e. on the order of 5 femtoMoles/min/cell) to 10 times the oxygen consumed by the cells in the cell containment system. The preferred range of pressures for hydrogen gas being supplied by electrolyzer 400 (out of cathode port 443) is 0-100 mmHg above ambient pressure. The preferred range of hydrogen flow rates being supplied to the cell containment system is 2 times the oxygen flow rate.

Electrolyzer device 400 is powered by a rechargeable or non-rechargeable coin battery located below a battery cover 442-2, which can be unscrewed from an electrolyzer housing top 410 for the purpose of replacing the battery. In an alternative embodiment, a larger energy compartment outside the body may supply energy to a rechargeable battery located beneath battery cover 442-2. The larger energy compartment outside the body may comprise a rechargeable or non-rechargeable battery (e.g. alkaline battery) located in a housing or battery pack, and transfer energy to the rechargeable battery internal to the electrolyzer device via electrical wiring. In another alternative embodiment, the energy compartment may be located outside of the body and may use rechargeable or non-rechargeable batteries (e.g. alkaline batteries) to transfer energy via electrical wiring to positive and negative terminals in the electrolyzer device (i.e. there is no internal battery in the electrolyzer device). In yet another embodiment, the energy supply may comprise a system for transcutaneous energy transfer wherein an external power source (e.g. rechargeable or non-rechargeable battery) coupled to a magnetic coil located outside the body transfers charge to a magnetic coil and/or battery internally located within the electrolyzer device.

Figure 5:
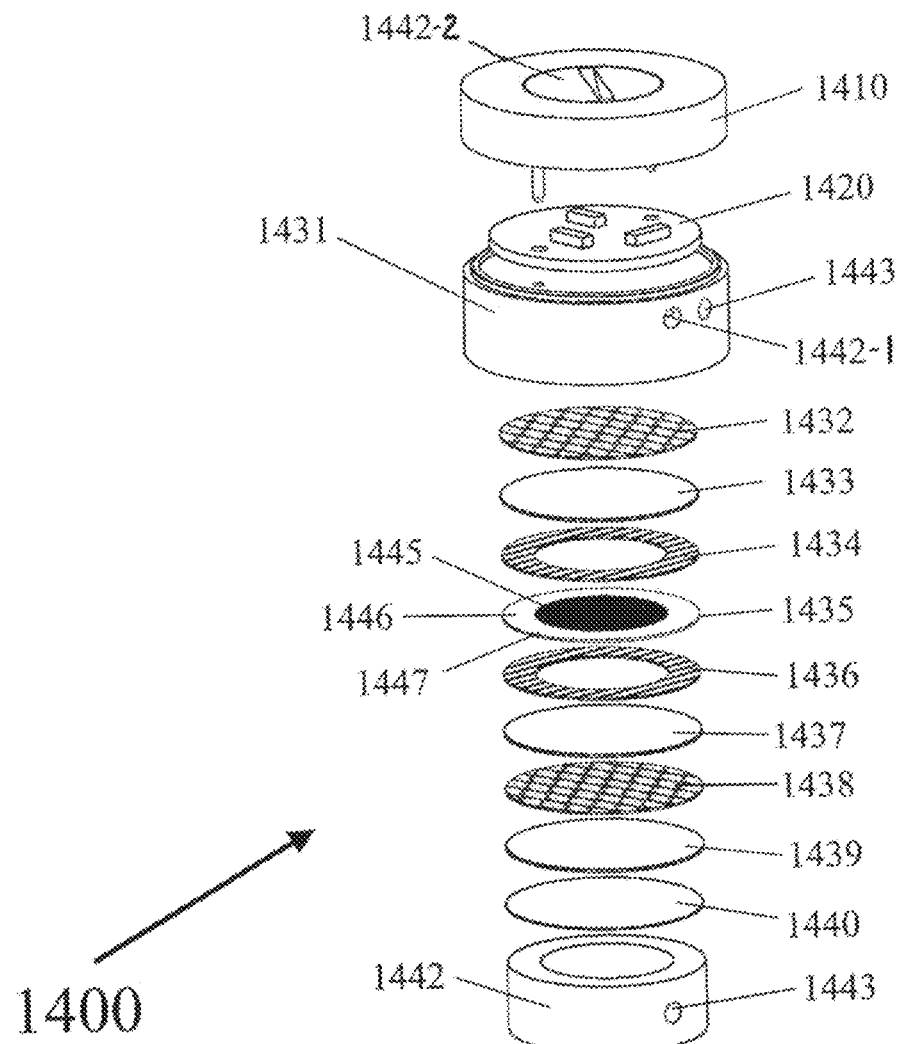
FIG. 5 is an exploded perspective view of another embodiment of an electrolyzer device that may be used in the system of FIG. 1 as the electrochemical device.

An exploded view of yet another embodiment of an electrolyzer device that may be used in system 100 as the electrochemical device is shown in FIG. 5 and is represented generally by reference numeral 1400. Electrolyzer device 1400 comprises several internal components identical or similar to electrolyzer device 400. For example, electrolyzer device 1400 comprises an electrolyzer housing top 1410, an electronics board 1420, a housing bottom 1431, a support mesh 1432, a vapor transport membrane 1433, a current collector 1434, a membrane electrode assembly (MEA) 1435, a current collector 1436, a vapor transport membrane 1437, a support mesh 1438, a vapor transport membrane 1439, a bio-compatible membrane 1440, an anode port 1442-1, a battery cover 1442-2, a cathode port 1443, an anode 1445, a proton-exchange membrane (PEM) 1446, and a cathode 1447. In contrast with electrolyzer device 400, electrolyzer device 1400 does not have a retaining ring (441 in electrolyzer device 400). Instead, electrolyzer device 1400 may comprise a water reservoir bottom 1442 wherein the water contained inside is bound by water reservoir bottom 1442 and a bio-compatible membrane 1440. The water inside the reservoir may be refilled using a sealable side access port 1443. In a further embodiment, the water reservoir may be filled with $H_2O^{17}$ wherein the electrolysis of $H_2O^{17}$ produces $O_2^{17}$ that is delivered to the cell containment system.

Figure 6:
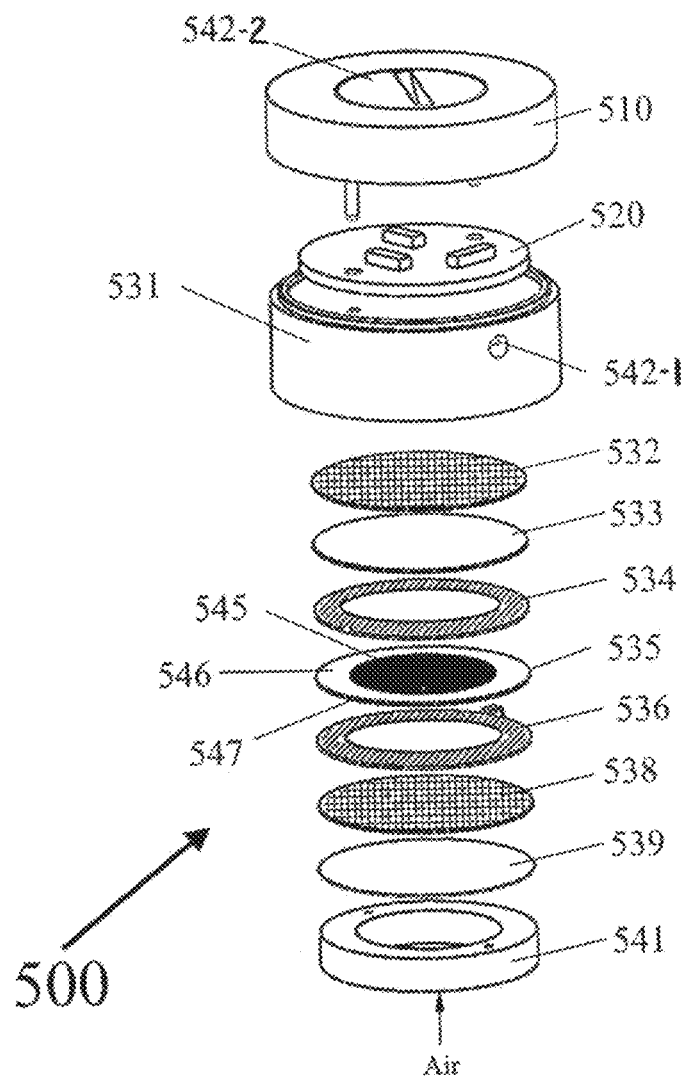
FIG. 6 is an exploded perspective view of one embodiment of an electrochemical oxygen concentrator (EOC) device that may be used in the system of FIG. 1 as the electrochemical device.

Referring now to FIG. 6, there is shown an exploded perspective view of an electrochemical oxygen concentrator (EOC) device that may be used in system 100 as the electrochemical device, the EOC device being represented generally by reference numeral 500. EOC device 500 is a proton-exchange membrane (PEM) based system that concentrates oxygen from air. Air enters the cathode side of EOC device 500 via the hole in retaining ring 541. The air source is ambient air.

Air diffusing through the cathode side of EOC device 500 is electrochemically concentrated into $O_2$ on the anode side of a membrane electrode assembly (MEA) 535. MEA 535 may comprise a proton-exchange membrane (PEM) 546 (e.g. NAFION" perfluorinated ion-exchange membrane, SOLVAY® proton-exchange membrane, AQUIVION® perfluorosulfonic acid ionomer membrane) with an air-depolarized cathode 547 (e.g. platinum-black, platinum on carbon, iridium, iridium oxide, ruthenium oxide) adhered to the bottom of PEM 546, and an anode 545 (e.g. platinum-black, platinum on carbon, iridium, iridium oxide, ruthenium oxide) adhered to the top of PEM 546. During electrochemical concentration of $O_2$ from air, substantially pure $O_2$ and $H^+$ ions are generated at the anode during the anode half-reaction (i.e. $2H_2O \rightarrow O_2+4H^++4e^-$). The potential difference between the two electrodes (generated by electronics board 520) drives $H^+$ ions from the anode to the air-depolarized cathode wherein the $H^+$ ions combine with electrons passing through the potentiostatic circuit (on electronics board 520) and $O_2$ to form $H_2O$ at the air-depolarized cathode during the cathode half-reaction (i.e. $O_2+4H^++4e^- \rightarrow 2H_2O$). During the electrochemical concentration of air into $O_2$, the air-depolarized cathode operates at a lower potential, preferably 0.7-1.2V, wherein the air-depolarized cathode is substantially free of $H_2$ production.

In the EOC device 500 stack-up, vapor transport membranes 533 and 539 provide gas access to MEA 535, but also act as a barrier to prevent contaminant liquids from reaching MEA 535. Examples of these vapor transport membranes 534 and 539 include, but are not limited to, ZITEX® porous polytetrafluoroethylene, GORE-TEX® expanded polytetrafluoroethylene, silicone rubber, PTFE, and TEFLON® polytetrafluoroethylene. Current collectors 534 (i.e. positive terminal) and 536 (i.e. negative terminal) provide electrical connections to the potentiostatic circuit located on electronics board 520. Current collectors 534 and 536 may comprise a conductive, corrosion-resistant metal, including, but not limited to, a metal from the valve metal group (Ti, Nb, Zr, Ta) or a metal from the noble metal group (Pt, Au, Pd). Support meshes 532 and 538 provide rigidity to the component stack-up and act to evenly distribute the load over the entire MEA surface area. Support meshes 532 and 538 may also comprise a conductive, corrosion-resistant metal, including, but not limited to, a metal from the valve metal group (Ti, Nb, Zr, Ta) or a metal from the noble metal group (Pt, Au, Pd).

$O_2$ gas generated by EOC device 500 flows out of an anode port 542-1 in a housing bottom 531. The preferred range of oxygen concentrations supplied by EOC device 400 (out of anode port 542-1) is 97-100% oxygen gas. The preferred range of pressures for oxygen gas being supplied is 0-100 mmHg above ambient pressure. The preferred range of oxygen flow rates being supplied to the cell containment system is one-tenth the oxygen consumed by the cells in the cell containment system (5 femtoMoles/min/cell) to 10 times the oxygen consumed by the cells in the cell containment system.

EOC device 500 is powered by a rechargeable or non-rechargeable coin battery located below a battery cover 542-2, which can be unscrewed from an EOC housing top 510 for the purpose of replacing the battery when necessary. In an alternative embodiment, a larger energy compartment may supply energy to a rechargeable battery located beneath battery cover 542-2. The larger energy compartment may comprise a rechargeable or non-rechargeable battery (e.g. alkaline battery) located in a housing or battery pack, and transfer energy to the rechargeable battery internal to the EOC device via electrical wiring. In yet another embodiment, the energy supply may comprise a system for transcutaneous energy transfer wherein an external power source (e.g. rechargeable or non-rechargeable battery) coupled to a magnetic coil located outside the body transfers charge to a magnetic coil and/or battery internally located within the EOC device.

Referring now to FIG. 7a, there is shown one embodiment of a cell containment system that may be used in system 100, the cell containment system being represented generally by reference numeral 600. Oxygen and hydrogen gas are delivered from the electrolyzer device to cell containment system 600 via an $O_2$ supply tube 602 and a $H_2$ supply tube 603. The two gas supply tubes may comprise any non-porous tubing, including, but not limited to, TEFLON® polytetrafluoroethylene, polypropylene, polycarbonate, and tygon. Ultrasonic welding may be used to secure the gas supply tubes within an exterior wall 604. Alternatively, the supply tubes may be secured within the exterior wall using medical grade epoxy, standard tube fittings (e.g. barbed, Luer lock, and SWAGELOK® compression fittings), or overmolding. As oxygen and hydrogen gas flow into an interior compartment 601, the gases flow into an $O_2$ delivery tube 606 and an $H_2$ delivery tube 607, respectively. The delivery tubes may comprise permeable tubing (e.g. NAFION® perfluorinated ion-exchange membrane, GORE-TEX® expanded polytetrafluoroethylene, and silicone rubber tubing). To prevent excess gas build-up in the gas delivery system, an $O_2$ venting tube 611 and an $H_2$ 612 venting tube are connected on one end to $O_2$ delivery tube 606 and $H_2$ delivery tube 607 wherein excess gas flows out of the other end of the two venting tubes located above the surface of the skin. In interior compartment 601, the two gas delivery tubes 606 and 607 overlay the two gas supply tubes 602 and 603 and the two gas venting tubes 611 and 612 wherein the ends are secured together using medical grade epoxy. Alternatively, the ends of the tubes may be secured together using ultrasonic welding or standard tube fittings (e.g. barbed, Luer lock, and SWAGELOK® compression fittings). The venting tubes may comprise tubing identical or similar to the supply tubes, and may be secured within exterior wall 604 by the same means as the supply tubes.

Cells are transferred into cell containment system 600 using a sealable cell transfer tube 605. Cell transfer tube 605 may comprise tubing identical or similar to supply tubes 602 and 603, and may be secured within exterior wall 604 by the same means as the supply tubes. Sealable cell transfer tube 605 may be sealed with medical grade epoxy, ultrasonically welded together, clamped, or sealed using an insert piece of polymer or plastic. Sealable cell transfer tube 605 may be used to transfer cells after implantation of the cell containment device. For instance, the cell containment device may be first implanted without cells in order to pre-vascularize the cell containment device wherein the cells are later transferred into the cell containment device using the cell transfer tube.

Referring now to FIG. 7b, it can be seen that cells 610 fill interior compartment 601, and surround $O_2$ delivery tube 606 and $H_2$ delivery tube 607. Interior compartment 601 is bound by exterior walls 604. Exterior walls 604 are formed by ultrasonically welding together two pieces of a composite membrane at the edges to form a pouch-like shape. Alternatively, the two pieces of a composite membrane comprising exterior walls 604 may be secured at the edges using medical grade epoxy or hot-pressing. In yet another alternative, the composite membrane comprising exterior wall 604 may be molded as one continuous piece. For efficient gas distribution to cells, the dimensions of interior compartment 601 (bound by exterior walls 604) are preferably 20 cm or less in length, 20 cm or less in width, and 3 mm or less in height.

Exterior walls 604 may comprise a composite of selectively permeable membrane 608 and vascularizing membrane 609. Selectively permeable membrane 608 may comprise a membrane that prevents bio-fouling, does not let cells pass through said selectively permeable membrane, but allows liquids and gases to pass through said selectively permeable membrane. Examples of the selectively permeable membrane include, but are not limited to, expanded PTFE with a pore size of 0.5 µm or less. The preferred thickness of the selectively permeable membrane is 30-50 µm. Vascularizing membrane 609 may comprise a membrane that allows for the growth and presence of the microvasculature within said vascularizing membrane, but the microvasculature does not penetrate selectively permeable membrane 604. An example of this vascularizing membrane is expanded PTFE with at least some of the pores being 3 µm or greater in diameter. The preferred thickness range of the vascularizing membrane is 30-50 µm. In an alternative embodiment, exterior walls 604 may comprise a single vascularizing membrane that allows the microvasculature to penetrate into interior compartment 601, but does not allow the interior cells, particularly cell clusters (e.g. islets), pass through the membrane. An example of this single membrane is expanded PTFE with at least some of the pores being 3 µm or greater in diameter. The preferred thickness range of this single membrane is 30-50 µm.

Cells 610 that fill interior compartment 601 may comprise one or more of the following categories: individual cells, individual cells contained within a matrix, microencapsulated cells, aggregated cells, clusters of cells including, but not limited to, islets, tissue, or artificial tissue constructs that fit within the interior compartment. Cells 610 may further comprise cells contained within a matrix, including, but not limited to, hydrogel, sodium alginate, and agarose. The cell matrix may further comprise other active compounds, including, but not limited to, immunomodulators, immunoprotectants, nutrients, antioxidants, chemicals that prevent bio-fouling, chemicals that induce or prevent vascularization, and chemicals that store oxygen (e.g. perfluorocarbons).

The cells comprising 610 may provide one or more biological functions. One biological function may be filling space with fat or muscle cells after surgical removal of native tissue. Alternatively, the cells comprising 610 may secrete therapeutic agents (e.g. dopamine, human growth factor, insulin, pain-relieving analgesics) either constitutively or in a physiologic feedback manner. The types of cells 610 may include, but are not limited to, primary cells, cultured cell lines, engineered cells or cell lines, adult or embryonic stems cells, and pluripotent cells. The source of cells 610 may be from any mammalian species, including, but not limited to, human, porcine, bovine, or rodent. Alternatively, the cells may originate from non-mammalian species, such as bacteria or algae.

In yet another alternative, cells 610 may comprise all varieties of pancreatic islets, including, but not limited to, various mammalian species (e.g. porcine, human, rodent, and non-human primate) and developmental stages (e.g. adult, juvenile, and neonatal). Cells 610 may further comprise the alpha and/or beta cells of pancreatic islets, or cells engineered to perform similar functions.

The preferred range of cellular packing densities within compartment 601 is from high densities (e.g. on the order of $1 \times 10^9$ cell/ml) to low densities (e.g. on the order of $1 \times 10^3$ cells/ml). In the case of pancreatic islets located within the interior cell compartment of the cell containment system, the preferred range of islet packing density is 100-10,000 human islet equivalents per kilogram of the recipient's body weight. If the islets are porcine islets located within the interior cell compartment of the cell containment system, the preferred range of porcine islet cell packing density is 25,000-100,000 porcine islet equivalents per kilogram of the recipient's body weight.

Referring now to FIG. 8a, there is shown another embodiment of a cell containment system that may be used in system 100, the cell containment system being represented generally by reference numeral 700. Oxygen and hydrogen gas are delivered from the electrolyzer device to cell containment system 700 via an $O_2$ supply tube 702 and an $H_2$ supply tube 703. The two gas supply tubes may comprise tubing identical or similar to $O_2$ and $H_2$ supply tubes 602 and 603, and may be secured within an exterior wall 704 by the same means used to secure $O_2$ and $H_2$ supply tubes 602 and 603 within exterior wall 604. As oxygen and hydrogen gas flow into interior compartment 701, the gases flow into $O_2$ delivery tube 706 and $H_2$ delivery tube 707, said delivery tubes spanning approximately the entire length of interior compartment 701. The delivery tubes may comprise permeable tubing (e.g. NAFION® perfluorinated ion-exchange membrane, GORE-TEX® expanded polytetrafluoroethylene, and silicone rubber tubing) wherein oxygen and hydrogen gas diffuse out of the delivery tubes and into the surrounding cells. Oxygen and hydrogen gas may also flow out of the open ends of the delivery tubes. In an alternative embodiment, to prevent excess gas build-up $O_2$ delivery tube 706 and $H_2$ delivery tube 707 may be connected to venting tubes by the same means used to connect $O_2$ and $H_2$ delivery tubes 606 and 607 to $O_2$ and $H_2$ venting tubes 611 and 612. The venting tubes may comprise tubing identical or similar $O_2$ and $H_2$ venting tubes 611 and 602, and the means of securing said venting tubes within exterior wall 704 may be identical or similar to the means used to secure $O_2$ and $H_2$ venting tubes 611 and 612 to exterior wall 604.

Cell containment system 700 may further comprise a nutrient supply tube 709 used to deliver active compounds (e.g. $N_2$, $CO_2$, NO, nutrients, growth factors, and hormones) to the cells from an external source. The sealable end of nutrient supply tube 709 is used to feed nutrients into said delivery tube with said sealable end located above or just below the surface of the skin. The nutrient delivery tube may comprise tubing identical or similar to $O_2$ and $H_2$ supply tubes 702 and 703, and the means of securing said nutrient supply tube to exterior wall 704 may be identical or similar to the means used to secure $O_2$ and $H_2$ supply tubes 702 and 703 to exterior wall 704. The nutrients supplied from the external source flow from nutrient supply tube 709 into nutrient delivery tube 711. In interior compartment 701, nutrient delivery tube 711 overlays nutrient supply tube 709, and the ends are secured together using medical grade epoxy. Alternatively, the ends of the tubes may be secured together using ultrasonic welding or standard tube fittings (e.g. barbed, Luer lock, and SWAGELOK® compression fittings). Nutrient delivery tube 711 may comprise gas or liquid permeable tubing (e.g. NAFION" perfluorinated ion-exchange membrane, GORE-TEX® expanded polytetrafluoroethylene, and silicone rubber tubing) wherein nutrients diffuse out of the delivery tubes and into the surrounding cells. Nutrients may also flow out of the open ends of the delivery tube.

Still referring to FIG. 8a, cells are transferred into cell containment system 700 using a sealable cell transfer tube 705. Cell transfer tube 705 may comprise tubing identical or similar to cell transfer tube 605, and may be secured within exterior wall 704 by the same means used to secure cell transfer tube 605 to exterior wall 604.

Referring now to FIG. 8b, it can be seen that cells 710 fill interior compartment 701, and surround $O_2$ delivery tube 706, $H_2$ delivery tube 707, and nutrient delivery tube 711. Cells 710 may comprise cells identical or similar to cells 610.

Interior compartment 701 is bound by exterior walls 704, said exterior walls formed by the same means used to form exterior walls 604. For efficient gas and nutrient distribution to cells 710, the dimensions of the interior compartment 701 are preferably 20 cm or less in length, 20 cm or less in width, and 3 mm or less in height.

Exterior walls 704 may comprise a single vascularizing membrane that allows the microvasculature to penetrate into interior compartment 701, but does not allow the interior cells, particularly cell clusters (e.g. islets), pass through the membrane. An example of this membrane is expanded PTFE with at least some of the pores being 3 µm or greater in diameter. The preferred thickness range of this single membrane is 30-50 µm. In an alternative embodiment, exterior walls 704 may comprise a composite of two membranes identical or similar to the composite of two membranes used to form exterior walls 604.

Referring now to FIG. 9a, there is shown another embodiment of a cell containment system that may be used in system 100, the cell containment system being represented generally by reference numeral 800. Oxygen and hydrogen gas are delivered from the electrolyzer device to cell containment system 800 via an $O_2$ supply tube 812 and an $H_2$ supply tube 813. The two gas supply tubes may comprise tubing identical or similar to $O_2$ and $H_2$ supply tubes 602 and 603, and may be secured within exterior walls 804 by the same means used to secure $O_2$ and $H_2$ supply tubes 602 and 603 within exterior wall 604. Cells are transferred into cell containment system 800 using a sealable cell transfer tube 805. Cell transfer tube 805 may comprise tubing identical or similar to cell transfer tube 605, and may be secured within exterior wall 804 by the same means used to secure cell transfer tube 605 to exterior wall 604.

Referring now to FIG. 9b, cell containment system 800 may comprise internal cell compartment 801 and internal gas compartment 802. Cells 810 contained within internal cell compartment 801 may comprise cells identical or similar to cells 610. For efficient gas distribution to cells 810, the dimensions of internal cell compartment 801 are preferably 20 cm or less in length, 20 cm or less in width, and 1 mm or less in height. The dimensions of internal gas compartment 802 are preferably 20 cm or less in length, 20 cm or less in width, and 3 mm or less in height.

Both the internal cell compartment and the internal gas compartment are bound by exterior walls 804 and selectively permeable membrane 803. Exterior walls 804 may comprise a single vascularizing membrane identical or similar to the single membrane used to form exterior walls 704. In an alternative embodiment, exterior walls 804 may comprise a composite of two membranes identical or similar to the composite of two membranes used to form exterior walls 604.

Selectively permeable membrane 803 may comprise a composite of support membrane 815 and cell isolation membrane 816. Support membrane 815 may comprise a permeable membrane that also provides rigidity to cell isolation membrane 816. Examples of the support membrane include, but are not limited to, expanded PTFE with a pore size of 3 µm or greater, silicone rubber, TEFLON® polytetrafluoroethylene, and GORE-TEX® expanded polytetrafluoroethylene. The preferred thickness range of the support membrane is 30-50 µm. Cell isolation membrane 803 may comprise a gas-only permeable membrane that prevents cells and liquids in internal cell compartment 801 from passing into internal gas compartment 802. Examples of the cell isolation membrane include, but are not limited to, silicone rubber, TEFLON® polytetrafluoroethylene, and GORE-TEX® expanded polytetrafluoroethylene. The preferred thickness range of the cell isolation membrane is 30-50 µm. Support membrane 815 and cell isolation membrane 816 membranes may be bonded together using hot-pressing or ultrasonic welding. In an alternative embodiment, selectively permeable membrane 803 may comprise a single permeable membrane that allows gas and liquids to pass through the membrane, but prevents cells in internal cell compartment 801 from passing into internal gas compartment 802. An example of this single membrane includes, but is not limited to, expanded PTFE with a pore size of 3 µm or greater in diameter. The preferred thickness range of this single membrane is 30-50 µm.

Figure 9C:
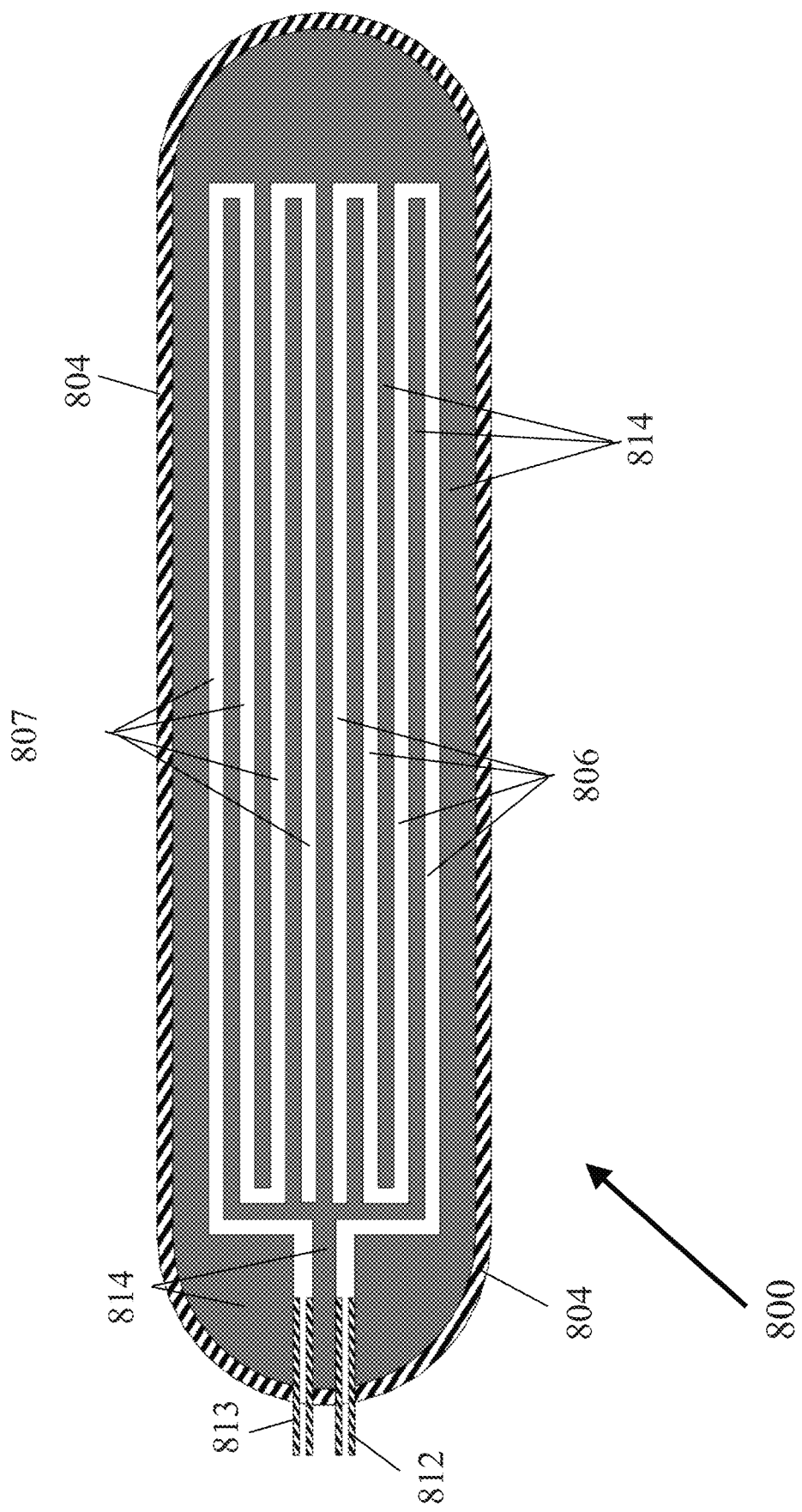
FIG. 9*c* is section view of the cell containment system of FIG. 9*b* taken along line 2-2 to reveal the construction of the gas compartment.

To prevent the mixing of oxygen and hydrogen gas in internal gas compartment 802, $O_2$ supply tube 812 and $H_2$ supply tube 813 deliver oxygen and hydrogen gas to isolated $O_2$ delivery channels 806 and isolated $H_2$ delivery channels 807, respectively. Referring now to FIG. 9c, it can be seen that isolated $O_2$ delivery channels 806 and isolated $H_2$ delivery channels 807 of gas compartment 802 each form a serpentine path bounded by gas impermeable walls 814. Gas impermeable walls 814 may comprise any gas impermeable plastic or polymer (e.g. polypropylene, TEFLON® polytetrafluoroethylene, polycarbonate, and polysulfone). The gas impermeable walls may be molded as one continuous piece, or machined out of one continuous block of polymer/plastic. Alternatively, the gas impermeable walls may comprise multiple pieces molded or machined polymer/plastic that are ultrasonically welded together, or epoxied together with a medical grade epoxy. In an alternative embodiment, internal gas compartment 802 may comprise at least one isolated $O_2$ delivery channel, at least one isolated $H_2$ delivery channel, and at least one gas impermeable wall separating the isolated $O_2$ delivery channel(s) from the isolated $H_2$ delivery channel(s). To prevent excess gas build-up in the gas delivery channel(s), this alternative embodiment may further comprise venting tubes secured to exterior walls 804 (with access to the isolated delivery channels) by the same means used to secure $O_2$ supply tube 812 and $H_2$ supply tube 813 to exterior walls 804 (with access to the isolated delivery channels). The venting tubes may comprise tubing identical or similar to $O_2$ venting tube 611 and $H_2$ venting tube 612 with the open ends of the venting tubes located above the surface of the skin.

Figure 10A:
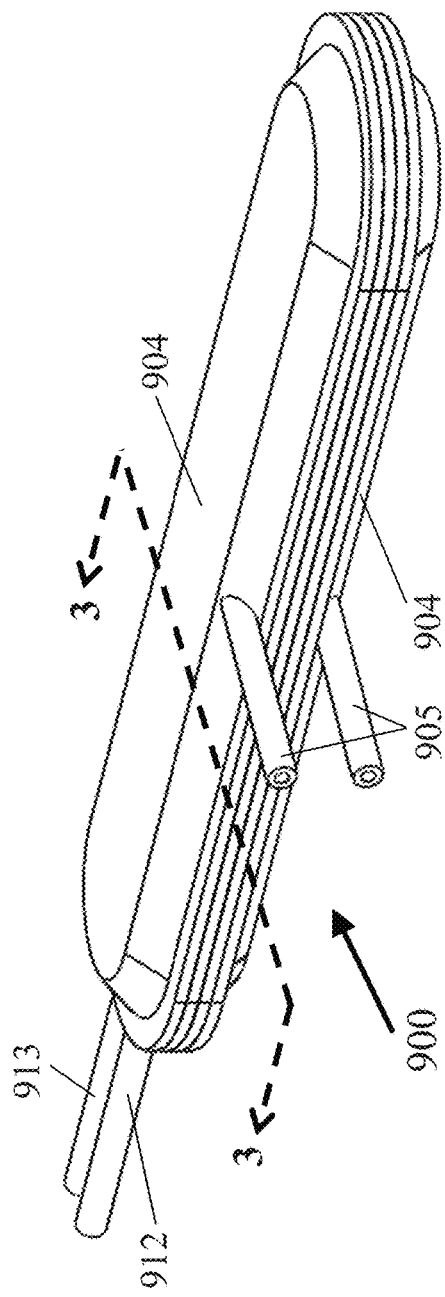
FIG. 10*a* is a perspective view of another embodiment of a cell containment system that may be used in the system of FIG. 1.

Referring now to FIG. 10a, there is shown another embodiment of a cell containment system that may be used in system 100, the cell containment system being represented generally by reference numeral 900. Oxygen and hydrogen gas are delivered from the electrolyzer device to cell containment system 900 via an $O_2$ supply tube 912 and an $H_2$ supply tube 913. The two gas supply tubes may comprise tubing identical or similar to $O_2$ and $H_2$ supply tubes 602 and 603, and may be secured within exterior walls 904 by the same means used to secure $O_2$ and $H_2$ supply tubes 602 and 603 within exterior wall 604. Cells are transferred into cell containment system 900 using sealable cell transfer tubes 905. The cell transfer tubes may comprise tubing identical or similar to cell transfer tube 605, and may be secured within exterior wall 904 by the same means used to secure cell transfer tube 605 to exterior wall 604.

Figure 10B:
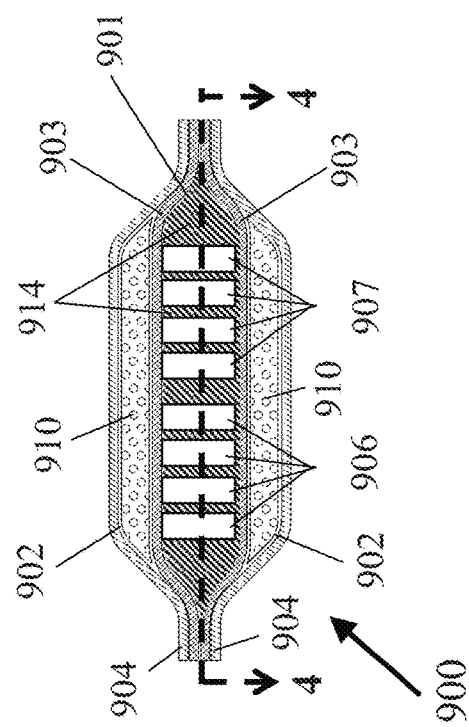
FIG. 10*b* is a section view of the cell containment system of FIG. 10*a* taken along line 3-3.

Referring now to FIG. 10b, it can be seen that cell containment system 900 may comprise internal gas compartment 902 sandwiched between internal cell compartments 901. Cells 910 contained within internal cell compartments 901 may comprise cells identical or similar to cells 610. For efficient gas distribution to cells 910, the dimensions of internal cell compartments 901 are preferably 20 cm or less in length, 20 cm or less in width, and 1 mm or less in height. The dimensions of internal gas compartment 902 are preferably 20 cm or less in length, 20 cm or less in width, and 3 mm or less in height.

Both internal cell compartments 901 are bound by exterior walls 904 and selectively permeable membranes 903. Internal gas compartment is bound on all sides by selectively permeable membranes 903. Exterior walls 904 may comprise a single membrane identical or similar to the single vascularizing membrane used to form exterior walls 704. In an alternative embodiment, exterior walls 904 may comprise a composite of two membranes identical or similar to the composite of two membranes used to form exterior walls 604.

Selectively permeable membranes 903 may comprise single permeable membranes that allow gas and liquids to pass through the membrane, but prevents cells, particularly cell clusters (e.g. islets), in internal cell compartments 901 from passing into internal gas compartment 902. An example of selectively permeable membrane includes, but is not limited to, expanded PTFE with a pore size of 1.0 µm or greater. The preferred thickness range of this selectively permeable membrane is 30-50 µm. In an alternative embodiment, selectively permeable membranes 903 may comprise a composite of two membranes identical or similar to the composite of two membranes that comprise selectively permeable membrane 803.

Figure 10C:
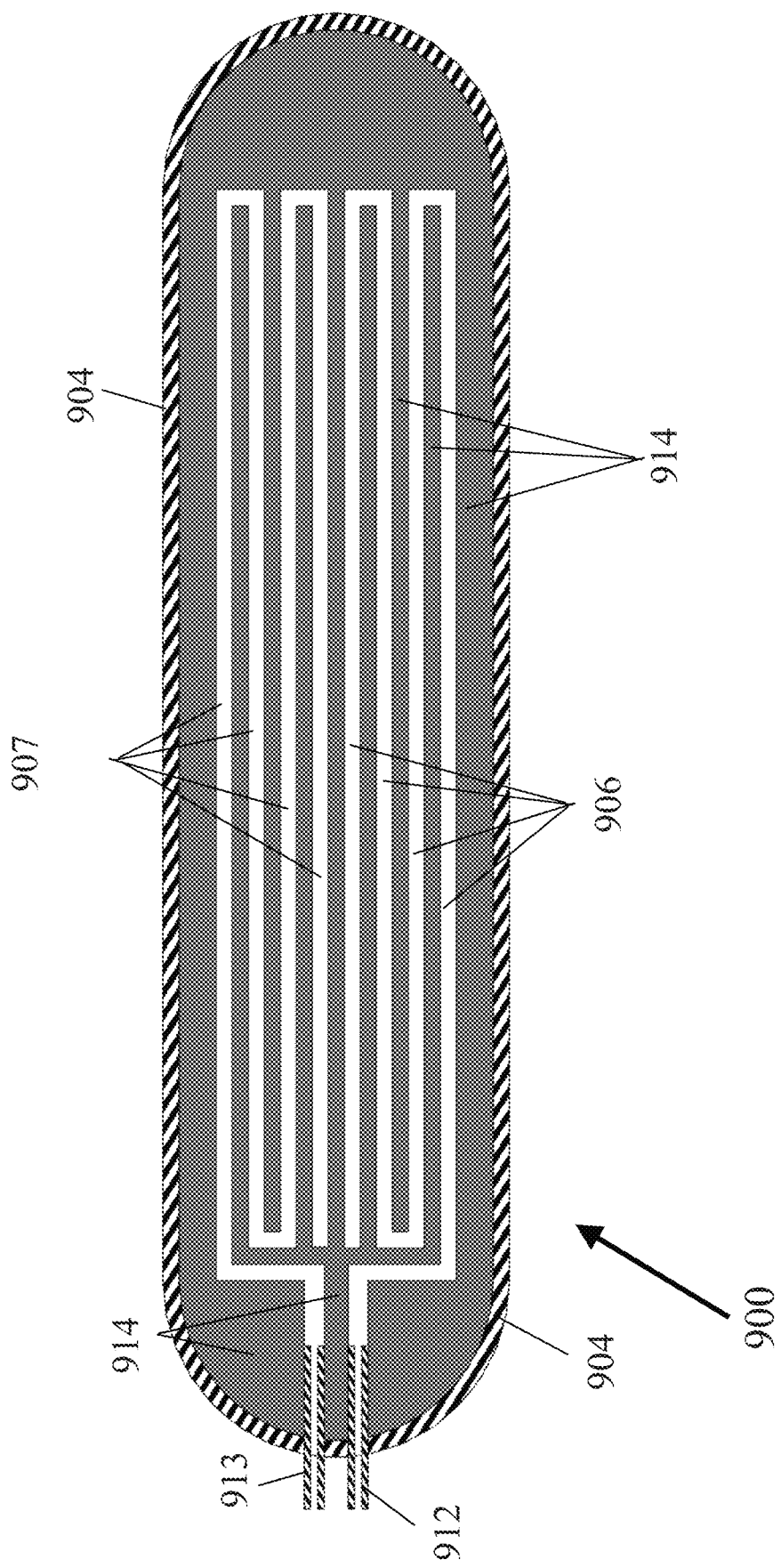
FIG. 10*c* is a section view of the cell containment system of FIG. 10*b* taken along line 4-4 to reveal the construction of the gas compartment.

To prevent the mixing of oxygen and hydrogen gas in internal gas compartment 902, $O_2$ supply tube 912 and $H_2$ supply tube 913 deliver oxygen and hydrogen gas to isolated $O_2$ delivery channels 906 and isolated $H_2$ delivery channels 907, respectively. Referring now to FIG. 10c, it can be seen that isolated $O_2$ delivery channels 906 and isolated $H_2$ delivery channels 907 in compartment 902 form a serpentine path bounded by gas impermeable walls 914. Gas impermeable walls 914 may comprise a material identical or similar to gas impermeable walls 914, and may be formed by the same means used to form gas impermeable walls 914. In an alternative embodiment, internal gas compartment 902 may comprise at least one isolated $O_2$ delivery channel, at least one isolated $H_2$ delivery channel, and at least one gas impermeable wall separating the isolated $O_2$ delivery channel(s) from the isolated $H_2$ delivery channel(s). To prevent excess gas build-up in the gas delivery channel(s), this alternative embodiment may further comprise venting tubes secured to exterior walls 904 (with access to the isolated delivery channels) by the same means used to secure $O_2$ supply tube 912 and $H_2$ supply tube 913 to exterior walls 904 (with access to the isolated delivery channels). The venting tubes may comprise tubing identical or similar to $O_2$ venting tube 611 and $H_2$ venting tube 612 with the open ends of the venting tubes located above the surface of the skin.

Figure 11A:
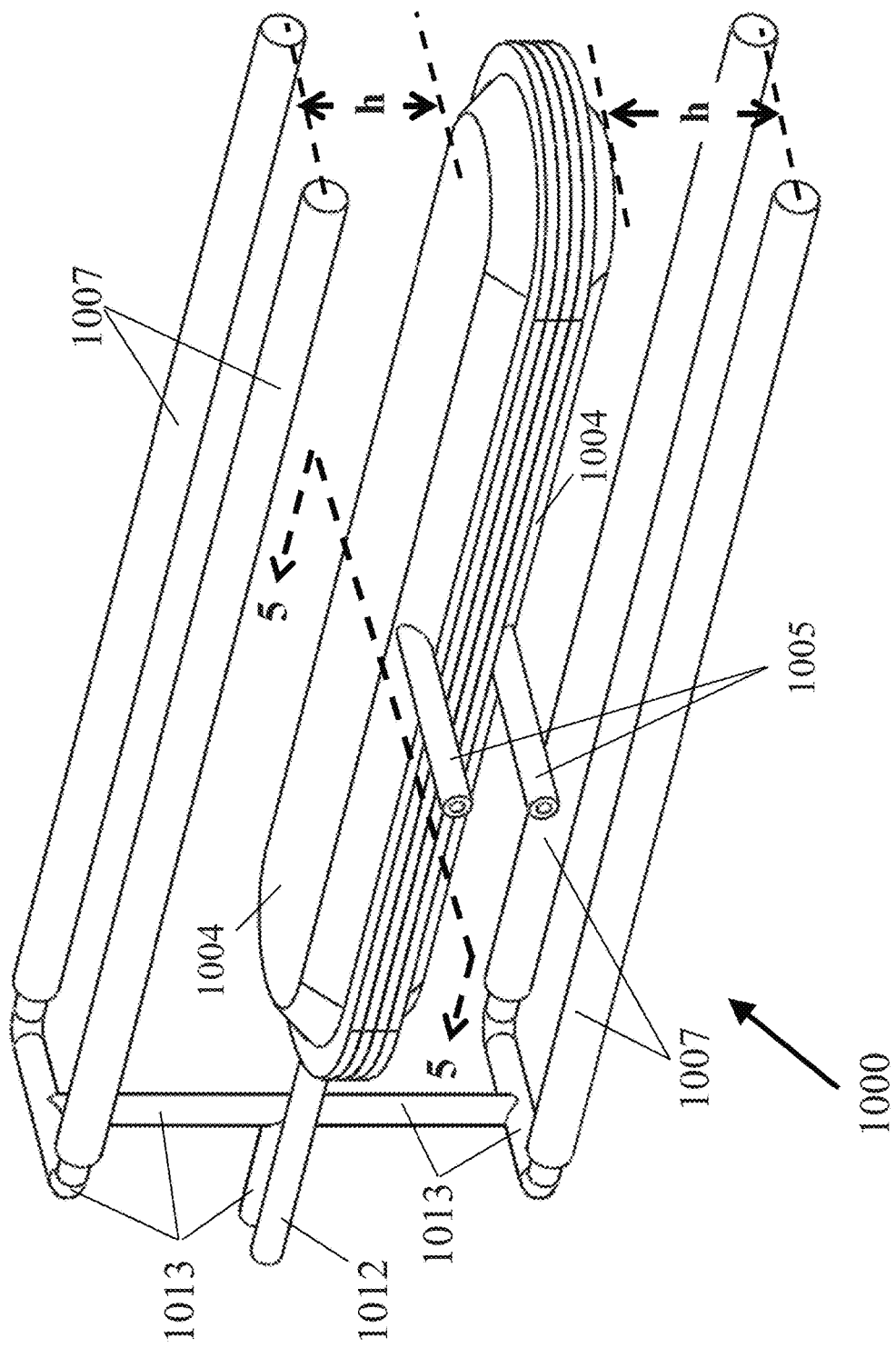
FIG. 11*a* is a perspective view of another embodiment of a cell containment system that may be used in the system of FIG. 1.

Referring now to FIG. 11a, there is shown another embodiment of a cell containment system that may be used in system 100, the cell containment system being represented generally by reference numeral 1000. Hydrogen gas is delivered from the electrolyzer device to the exterior of cell containment system 1000 using an impermeable $H_2$ supply manifold 1013. $H_2$ supply manifold 1013 may comprise a single impermeable tube from the outlet of the electrochemical device that branches into two tubes located above the cell containment system and two tubes located below the cell containment system. The $H_2$ supply manifold is molded as one continuous piece. Alternatively, the $H_2$ supply manifold may comprise segments of tube joined by medical grade epoxy or standard tube fittings (e.g. SWAGELOK® compression fittings, and Luer lock fittings), including, but not limited to, elbow connectors, union connectors, and t-connectors. $H_2$ delivery tubes 1007 are secured to the ends of each branch of $H_2$ supply manifold 1013 using medical grade epoxy. Alternatively, the $H_2$ delivery tubes may be secured to each branch of the $H_2$ supply manifold using ultrasonic welding or standard tube fittings (e.g. barbed, SWAGELOK® compression fittings, and Luer lock fittings). $H_2$ delivery tubes 1007 may comprise gas-permeable tubing (e.g. NAFION® perfluorinated ion-exchange membrane, GORE-TEX® expanded polytetrafluoroethylene, and silicone rubber tubing) located at a distance 'h' that is 0-5 mm above or below the surface of cell containment system 1000. Oxygen gas is delivered from the electrolyzer device to the interior of cell containment system 1000 using an $O_2$ supply tube 1012. The $O_2$ gas supply tube may comprise tubing identical or similar to $O_2$ supply tube 602, and may be secured within exterior walls 1004 by the same means used to secure $O_2$ supply tube 602 within exterior wall 604. Cells are transferred into cell containment system 1000 using sealable cell transfer tubes 1005. The cell transfer tubes may comprise tubing identical or similar to cell transfer tube 605, and may be secured within exterior wall 1004 by the same means used to secure cell transfer tube 605 to exterior wall 604.

Figure 11B:
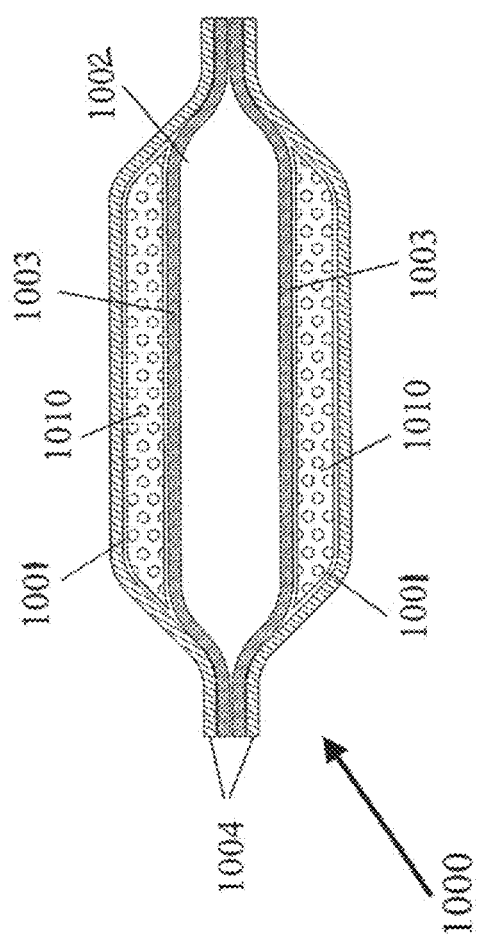
FIG. 11*b* is a section view of the cell containment system of FIG. 11*a* taken along line 5-5.

Referring now to FIG. 11b, cell containment system 1000 can be seen to comprise internal gas compartment 1002 sandwiched between internal cell compartments 1001. Cells 1010 contained within internal cell compartments 1001 may comprise cells identical or similar to cells 910. For efficient gas distribution to cells 1010, the dimensions of internal cell compartments 1001 are preferably 20 cm or less in length, 20 cm or less in width, and 1 mm or less in height. The dimensions of internal gas compartment 1002 are preferably 20 cm or less in length, 20 cm or less in width, and 3 mm or less in height.

Both internal cell compartments 1001 are bound by exterior walls 1004 and selectively permeable membranes 1003. Internal gas compartment 1002 is bound on all sides by selectively permeable membranes 1003. Exterior walls 1004 may comprise a single vascularizing membrane identical or similar to the single membrane used to form exterior walls 704. In an alternative embodiment, exterior walls 1004 may comprise a composite of two membranes identical or similar to the composite of two membranes used to form exterior walls 604.

Selectively permeable membranes 1003 may comprise single permeable membranes that allow gas and liquids to pass through the membrane, but prevent cells in internal cell compartments 1001 from passing into internal gas compartment 1002. An example of selectively permeable membrane includes, but is not limited to, expanded PTFE with a pore size of 1.0 µm or greater. The preferred thickness range of this selectively permeable membrane is 30-50 µm. In an alternative embodiment, selectively permeable membranes 1003 may comprise a composite of two membranes identical or similar to the composite of two membranes that comprise selectively permeable membrane 803.

According to the embodiments of the system for the gas treatment of cell implants described above, the following material describes the obstacles overcome by the present invention.

Cellular implants. There is a long history of research into cellular therapies, specifically encapsulated cellular implants. Encapsulation generally falls into two categories: micro-encapsulation and macro-encapsulation. In micro-encapsulation, cells or tissues are placed in a matrix (e.g. hydrogel) with relatively small quantities of cells per capsule. The matrix may or may not provide immunoprotection to the cells. The microcapsules are generally placed in the body (i.e. peritoneal cavity) and are not readily retrievable. In macro-encapsulation, there is generally a porous membrane surrounding (encapsulating) cells with or without a matrix surrounding the cells. The macro-encapsulation membrane may perform one or more functions, including keeping the implanted cells contained, immunoisolating the cells from the host immune system, helping the implant integrate into the body (vascularize), and facilitating the implant from becoming fully walled-off from the body by fibrosis. Macro-capsules are generally designed to be retrieved from the body for both safety and replacement. Generally, a single or small number of macro-capsules are intended for treatment. The present invention includes novel embodiments of the cell containment system described above that address many of the issues of current macro-encapsulating technology.

Macro-encapsulated implants generally have thin form factors (a sheet or a thin, tall cylinder) in acknowledgement of the fact that, in normal physiology, cells are within several hundred micrometers of a blood vessel supplying nutrients by diffusion. However, the thinnest dimensions typically have been larger than the optimal physiological distance, and the majority of implants have had necrotic cores of varying dimensions as seen by histological examination. These necrotic cores are the result of from cellular death in the central region. The limiting nutrient based on reaction diffusion models is generally considered to be oxygen (e.g. Avgoustiniatos, E. S. and C. K. Colton, Design considerations in immunoisolation, in *Principles of Tissue Engineering*, R. P. Lanza, R. Langer, and W. L. Chick, Editors. 1997, R. G. Landes: Austin, TX. p. 336-346.; Avgoustiniatos, E. S. and C. K. Colton, *Effect of external oxygen mass transfer resistances on viability of immunoisolated tissue*. Ann N Y Acad Sci, 831: p. 145-67, 1997) because of oxygen's low availability (partially due to its low solubility in aqueous solution) compared to other nutrients, such as glucose. The necrotic cores have been more extensive (larger in dimension) when the cellular density is great. In general, high cellular density is necessary for cellular implants to have the desired therapeutic effect, while remaining sufficiently compact in size, to be practical for surgical implant and for available implant sizes. Most reported studies of cellular implants typically have only been successful with low cellular densities. Low cellular density implants produce too low a dose of therapeutic compound to be pre-clinically or clinically effective. Higher cellular density implants have generally failed due to death of the implanted cells. In addition, there have been other causes of implant failure, such as ineffective immunoisolation membranes, tears in the cellular implant, and poor quality of cells prior to implant.

Cellular implants have been most extensively proposed for creating a bio-artificial pancreas (with islets or other insulin secreting and/or glucose regulating cells). However, cellular implants have been proposed and researched for the treatment of liver failure, Parkinson's disease (Luo X M, Lin H, Wang W, et al Recovery of neurological functions in non-human primate model of Parkinson's disease by transplantation of encapsulated neonatal porcine choroid plexus cells. *J Parkinsons Dis*. 2013 Jan. 1; 3(3):275-91), (para) thyroid disease, hemophilia, Alzheimer's, and pain control, as well as other conditions and diseases. Implants that secrete insulin, human growth hormone, dopamine, catecholamine, and other physiological active and/or therapeutic compounds have been attempted.

A brief background of the treatment options for Type 1 diabetes as well as an overview of attempts to create a bioartificial pancreas follow.

Diabetes affects approximately 25.8 million patients in the U.S. with about 5% of those cases being Type 1 diabetes (T1D). Standard treatment for T1D is patient glucose testing and multiple daily insulin injections. In addition, there are wearable insulin pumps and Continuous Glucose Monitoring (CGM) systems that partially automate the process and may result in better glucose control, thus minimizing the serious long term side effects of T1D (e.g. Bergenstal R M, Tamborlane W V, Ahmann A, et al. Effectiveness of sensor-augmented insulin-pump therapy in type 1 diabetes. *N Engl J Med,* 363:311-20, 2010). There is also progress towards a "closed-loop" system that would act as a mechanical artificial pancreas with automated insulin pump and CGM system (Klonoff, D. C., C. L. Zimliki, L. A. Stevens, P. Beaston, A. Pinkos, S. Y. Choe, G. Arreaza-Rubin, and W. Heetderks, *Innovations in technology for the treatment of diabetes: clinical development of the artificial pancreas (an autonomous system).* J Diabetes Sci Technol, 5(3): p. 804-26, 2011).

There are some T1D patients that have a high risk of death from hypoglycemic unawareness and brittle diabetes that are eligible for transplant of a cadaveric pancreas or pancreatic islets. In those severe forms of diabetes, the benefits outweigh the risks associated with necessarily lifelong immunosuppression regimes. It is estimated that there are approximately 300,000 brittle and/or hypoglycemic unaware diabetes patients, but only a fraction are getting the needed islet or pancreas transplants. In the past ten years, there have been significant advances in islet transplantation including the isolation and purification of human pancreatic islets. Pancreatic islet transplantation is available in a number of countries including Canada, United Kingdom, Australia, Switzerland and Germany. In the U.S. several medical centers are applying for an FDA biologics license application will be filed for the processed human pancreatic islet product following the completed NIH sponsored pivotal clinical trial.

A bio-artificial pancreas could be an alternative both for these high risk T1D patients as well as for T1D patents and potentially Type 2 Diabetes patients. An optimal bio-artificial pancreas could provide a number of advantages, including: a minor surgical procedure, natural glucose control, and no immunosuppression. The bio-artificial pancreas approach has the advantage of using islets that automatically sense glucose and produce insulin in order to meet physiological metabolic needs and reduce the complications of diabetes. The immunoisolation approach has several advantages, including: 1) protection from allotransplants and xenotransplants with little or no immunosuppression, 2) a simple surgical procedure to place implant ectopically (e.g. subcutaneously) without a complex surgical procedures, and 3) a retrievable device that can be removed in the event of complications, or to replace the cellular material as needed after several years, for example. The availability of insulin-producing stem cells and special virus-free porcine islet supplies are also becoming a near-term possibility; a limitless source of insulin producing cells would allow treatment of a much larger patient pool than could be treated with human cadaveric islets.

A brief summary of issues regarding islet transplantation and cellular transplants follows.

Overcoming barriers in islet transplantation. Recent promising islet transplantation results from leading centers using potent induction immunosuppression have demonstrated insulin independence for more than 5 years for 50% of the recipients (Bellin, M. D., F. B. Barton, A. Heitman, J. V. Harmon, R. Kandaswamy, A. N. Balamurugan, D. E. Sutherland, R. Alejandro, and B. J. Hering, *Potent induction immunotherapy promotes long-term insulin independence after islet transplantation in type* 1 *diabetes.* Am J Transplant, 12(6): p. 1576-83, 2012). However, widespread clinical application of allogeneic islet transplantation is hindered by two critical barriers: 1) the need for systemic immunosuppression for the current intraportal vein (liver) transplant site, and 2) the finite and low supply of human islet tissue (a few thousand suitable donors per year). For intraportal (liver) islet transplantation, it is estimated that >50% of the islets do not engraft or are lost within the first 8-10 weeks post-transplant (Ritz-Laser, B., J. Oberholzer, C. Toso, M. C. Brulhart, K. Zakrzewska, F. Ris, P. Bucher, P. Morel, and J. Philippe, *Molecular detection of circulating beta-cells after islet transplantation.* Diabetes, 51(3): p. 557-61, 2002). Thus, intraportal islet transplantation is an inefficient use of the limited supply of human islets.

The use of biocompatible, retrievable, cell implant systems may address these critical barriers in islet treatments for diabetes by enabling the more effective and efficient use of allogeneic islets without immunosuppression and the eventual use of stem cell-derived, or xenogeneic islets with minimum or no immunosuppression. In addition, there are patients who have their pancreata removed (for pancreatitis and pre-cancer diagnoses) who could also benefit from a simple transplant procedure with a cell implant system containing their own islets with or without immunoisolation.

Cellular implant devices. Cell implant macro-devices have been designed, fabricated, and tested for use with islets and other cell types Some, including TheraCyte, Inc.'s THERACYTE™ cell encapsulation device, have been successfully tested in small and large animal models (Tarantal, A. F., C. C. Lee, and P. Itkin-Ansari, Real-time bioluminescence imaging of macroencapsulated fibroblasts reveals allograft protection in rhesus monkeys (*Macaca mulatta*). Transplantation, 88(1): p. 38-41. 2009.) and, to a limited extent, in humans with excellent biocompatibility and safety profiles (Tibell, A., E. Rafael, L. Wennberg, J. Nordenstrom, M. Bergstrom, R. L. Geller, T. Loudovaris, R. C. Johnson, J. H. Brauker, S. Neuenfeldt, and A. Wernerson, *Survival of macroencapsulated allogeneic parathyroid tissue one year after transplantation in nonimmunosuppressed humans*. Cell Transplant, 10(7): p. 591-9, 2001). Devices have also demonstrated protection from allo- and auto-immunity with no immunosuppression in non-human primates with one study in human subjects and with xeno-immunity with low immunosuppression. However, work with large-animal models and islet sources more relevant to clinical application showing therapeutic efficacy is lacking. The rationale that enhanced oxygenation is essential for effective and practical cellular implants. The enhanced oxygenation for effective treatment of cellular implants is one of the obstacles overcome by the present invention.

Need for oxygen for high density cell implants. Scale-up of cell therapy devices for human use has been severely impaired by the device size requirements necessary for sufficient islet oxygenation to support islet viability and function (e.g. O'Sullivan, E. S., A. Vegas, D. G. Anderson, and G. C. Weir, *Islets transplanted in immunoisolation devices: a review of the progress and the challenges that remain*. Endocr Rev, 32(6): p. 827-44, 2011). Islets (especially islet β-cells) are particularly sensitive to hypoxia. In addition to its effect on islet viability, oxygen deprivation has a dramatic effect on islet function, as measured by glucose stimulated insulin secretion (GSIS). GSIS is an energy-dependent process and the threshold for oxygen effects is seen at oxygen levels 100-fold higher than those needed to affect viability.

Limitations of prevascularization approach, and the value of providing in situ oxygen generation. Immunoisolation devices prohibit cell-cell contact and the penetration of host blood vessels within the immunoisolation devices and within islets. If blood vessels were allowed to penetrate islets, that would eliminate the issue of oxygen supply, assuming that the islets were provided with sufficient oxygen to survive during the re-vascularization process (2-3 weeks post-transplant). Since this is not allowable in immunoisolation, alternative methods of supplying oxygen to the islets are critical. In pre-vascularization, blood vessels are allowed to form near or within the outer edge of the device prior to introduction of cells into the device. The THERACYTE™ cell encapsulation device is specifically designed to attract blood vessels into the outer membrane due to the pore structure of the membrane. This prevascularization may be enhanced by delivering a non-oxygen gas (e.g. N2, H2, CO2) to induce local hypoxia and induce vascularization at the molecular signaling level. However, it has been experimentally demonstrated that even with pre-vascularization, the islet loading in the device is still limited by the $pO_2$ that is available through the blood supply at the implantation site [10-40 mmHg or even lower] when metabolically active cells are transplanted (Goh, F., R. Long, Jr., N. Simpson, and A. Sambanis, *Dual perfluorocarbon method to noninvasively monitor dissolved oxygen concentration in tissue engineered constructs in vitro and in vivo*. Biotechnol Prog. 2011.; Goh, F. and A. Sambanis, *In vivo noninvasive monitoring of dissolved oxygen concentration within an implanted tissue-engineered pancreatic construct*. Tissue Eng Part C Methods, 17(9): p. 887-94, 2011).

Mathematical and diffusion modeling indicate that transplant site $pO_2$ (30 mmHg) at the device surface is insufficient to allow viability and function of pancreatic islets at an islet cell density greater than 1000 islet equivalents (IEQ) per $cm^2$ of macrocapsule surface area. These low density cellular loadings (1000 $IEQ/cm^2$) would require extremely large encapsulated cell implants (torso-sized). Use of biochemical agents to delay cellular death (e.g. anti-apopototic agents) during the hypoxia may decrease cellular death, but likely would impair cellular function long term. In the case of xenogeneic sources of islets, even higher device loadings may be necessary for xeno-transplantation since more porcine than human islets may be needed.

Cellular implants for diabetes—competing technologies. Cell therapy for diabetes is an area that has attracted the attention of a number of researchers and companies. Brief summaries of some technologies are provided below.

Sernova (London, ON, CAN) is currently utilizing a pre-vascularized implant device that is not immuno-protective. Therefore, the device allows blood vessels to grow within islets, which may enable sufficient oxygen supply assuming they survive the period of 2-3 weeks required for intra-islet vascularization. An initial allotransplant trial utilized immunosuppression.

ViaCyte, Inc. (San Diego, CA) is utilizing a device that is similar to the THERACYTE™ cell encapsulation device with stem cells. This device allows vascularization up to the immune-isolating membrane. It has no additional method of supplying oxygen.

Islet Sheet Medical uses a microencapsulation approach (i.e. an alginate sheet embedded with islets). While the company acknowledges the need for high islet density, the need for oxgyenation and the claim of 35% packing density it is not clear from the literature how this high packing density will receive sufficient oxygen (e.g. Krishnan, R., R. Arora, M. Lamb, O. Liang, S. M. White, A. Moy, R. Storrs, R. Dorian, S. King, C. Foster, E. Botvinick, B. Choi, and J. Lakey. *Vascular Remodeling in a Subcutaneous Site Secondary to Islet Transplantation and Biomaterial Implantation*. [cited 2012 Aug. 5]; Available from: http://www.hanumanmedicalfoundation.org/blog/wp-content/uploads/2012/07/201207-Rahul-TTS-poster.pdf).

Living Cell Technologies also uses a micro-encapsulation approach.

Beta-$O_2$ Technologies Ltd (Israel) has a technology that includes delivery of an oxygen supply via a line through the skin. The Beta-$O_2$ design for an implantable bio-artificial pancreas consists of an immunoisolating islet module with pancreatic islets inside an alginate hydrogel slab, and a gas chamber separated from the islet module by an oxygen permeable membrane (Ludwig, B., B. Zimerman, A. Steffen, K. Yavriants, D. Azarov, A. Reichel, P. Vardi, T. German, N. Shabtay, A. Rotem, Y. Evron, T. Neufeld, S. Mimon, S. Ludwig, M. D. Brendel, S. R. Bornstein, and U. Barkai, *A novel device for islet transplantation providing immune protection and oxygen supply*. Horm Metab Res, 42(13): p. 918-22. 2010.; Stern, Y., U. Barkai, A. Rotem, M. Reingewirtz, and Y. Rozy. *Apparatus for transportation of oxygen to implanted cells* USPTO, 8,043,271, 2008; Barkai, U., G. C. Weir, C. K. Colton, B. Ludwig, S. R. Bornstein, M. D. Brendel, T. Neufeld, C. Bremer, A. Leon, Y. Evron, K. Yavriants, D. Azarov, M. Zimermann, N. Shabtay, M. Balyura, T. Rozenshtein, P. Vardi, K. Bloch, P. de Vos, and A. Rotem, *Enhanced oxygen supply improves islet viability in a new bioartificial pancreas*. Cell Trans. 2012; Ludwig, B., A. Rotem, J. Schmid, G. C. Weir, C. K. Colton, M. D. Brendel, T. Neufeld, N. L. Block, K. Yavriyants, A. Steffen, S. Ludwig, T. Chavakis, A. Reichel, D. Azarov, B. Zimermann, S. Maimon, M. Balyura, T. Rozenshtein, N. Shabtay, P. Vardi, K. Bloch, P. de Vos, A. V. Schally, S. R. Bornstein, and U. Barkai, *Improvement of islet function in a bioartificial pancreas by enhanced oxygen supply and growth hormone releasing hormone agonist*. Proc Natl Acad Sci U S A, 109(13): p. 5022-7, 2012). Their results show that diabetic mice with implants and oxygen provision showed normal glycemic control for 6 months. When oxygen gas supply to the islet chamber was stopped, normoglycemic animals promptly became diabetic, thus demonstrating that oxygen was the limiting factor and the enhanced supply supported high density islet viability and function in vivo. In order for the pancreatic islets to remain viable for more than one or two days, the oxygen chamber was continually refilled. The researchers had to either inject 40% oxygen every 24 hours into the oxygen chamber or provide filtered atmospheric air via an external air tank and air pump for 15 minutes every 2 hours through subcutaneous access ports.

There is also research effort at University of Miami with an approach for a short-term chemical oxygen generation for temporary support of implants while they vascularize. (Pedraza, E., M. M. Coronel, C. A. Fraker, C. Ricordi, and C. L. Stabler, *Preventing hypoxia-induced cell death in beta cells and islets via hydrolytically activated, oxygen-generating biomaterials*. Proc Natl Acad Sci USA, 109(11): p. 4245-50, 2012). However, this approach cannot provide oxygen long-term (months/years) and is therefore limited as a bridge to vascularization.

The THERACYTE™ cell encapsulation device was originally developed by Baxter, Inc. for indications other than treatment of diabetes and one of its key features is an exterior facing membrane that promotes vascularization with a secondary membrane that is immunoisloating. The present invention is a novel alternative to the TheraCyte, Inc. commercial cell containment products. The present invention also includes an electrochemical gas generator. Originally, the three compartment version of the THERACYTE™ cell encapsulation device was utilized by Baxter for hemophilia applications with liquid flowing through the central chamber for transportation of factor VIII generated in the flanking chambers. TheraCyte publications also demonstrate the benefit of pre-vascularizing the device, and then later introducing the cells into the cell containment device.

Other Gases. While oxygen is generally known to be needed for cellular viability and function as described above, there are other gases that can be delivered to the cellular implant, or to the vicinity of the implant, that can provide benefits to the implant cells and/or the surrounding tissue. Gaseous hydrogen may act to protect cells by its antioxidant and antiapoptotic properties (see Wood et al., "The hydrogen highway to reperfusion therapy," Nature Medicine, 13(6): 673-4 (2007); Ohsawa et al., "Hydrogen acts as a therapeutic antioxidant by selectively reducing cytotoxic oxygen radicals," Nature Medicine, 13(6):688-94, 2007). Gaseous carbon dioxide may regulate metabolism and gaseous carbon monoxide may have anti-inflammatory and antiapoptotic effects (see Wang et al., "Donor Treatment with carbon monoxide can yield islet allograft survival and tolerance," Diabetes, 54(5):1400-6, 2005).

Figure 12:
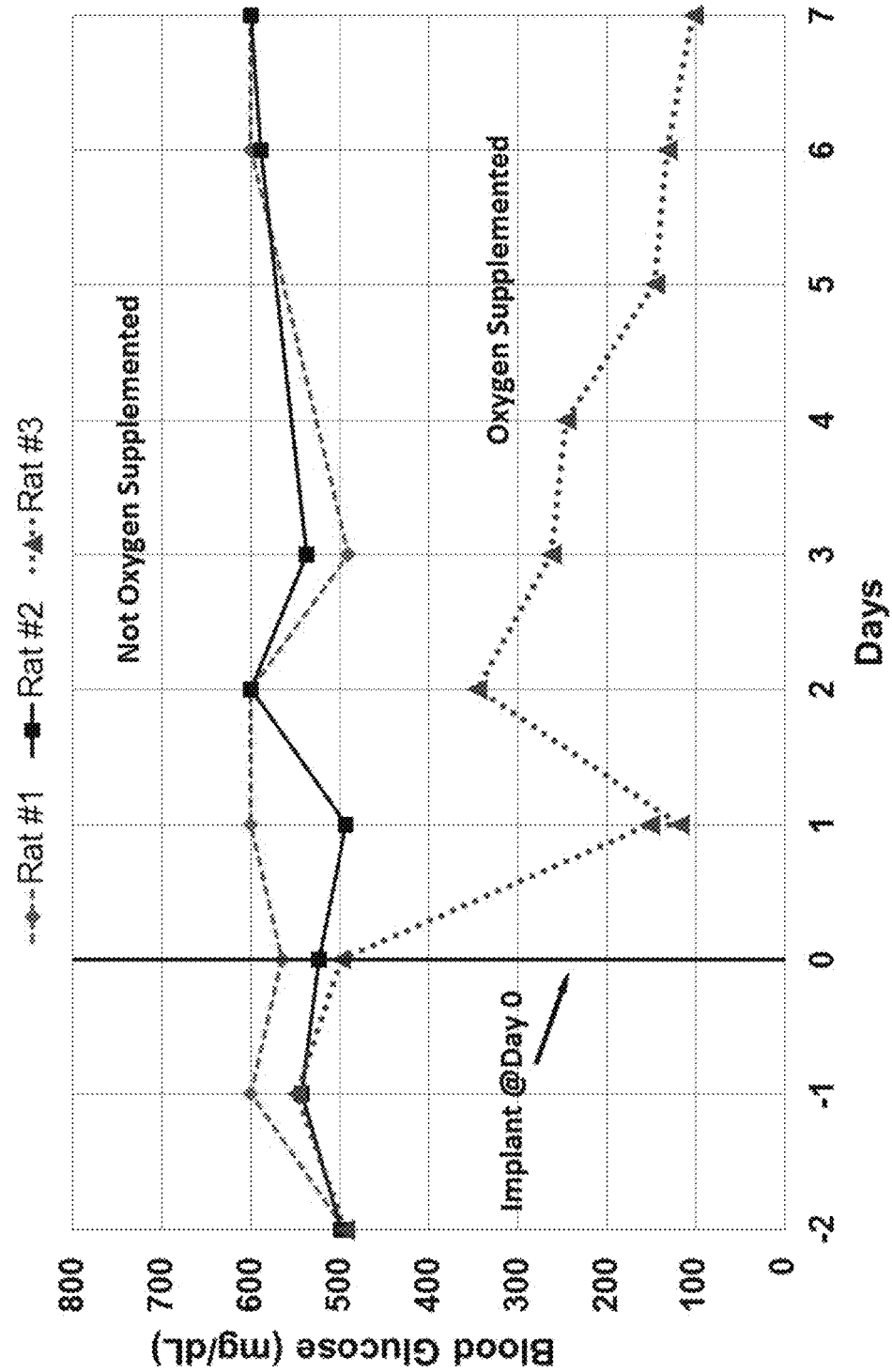
FIG. 12 is graph of experimental data illustrating a rat's blood glucose levels with and without oxygen treatment of the cells.

Example 1: Demonstration of the Efficacy of Oxygen Supply to a Cellular Implant in Rats. In a rat model with induced diabetes, 24,000 human islets were placed in each 3 cm$^2$ cell containment system. 40% oxygen from an externally located EOC was delivered to the center compartment of the cell containment system using an inlet with excess supply of oxygen (i.e. more oxygen than the known oxygen consumption rate of human islets). The cell containment system also had an outlet tube for venting any excess oxygen. Blood glucose was measured from the rats on a daily basis, including two days prior to implant. In the diabetic rats with devices that did not have oxygen supplementation, blood glucose remained at high, diabetic levels. In the rat with the oxygenated implant, blood glucose levels were reduced, thus indicating partial (150-350 mg/dL) to complete (<150 mg/dL) reversal of diabetes (see FIG. 12 for experimental results).

Figure 13:
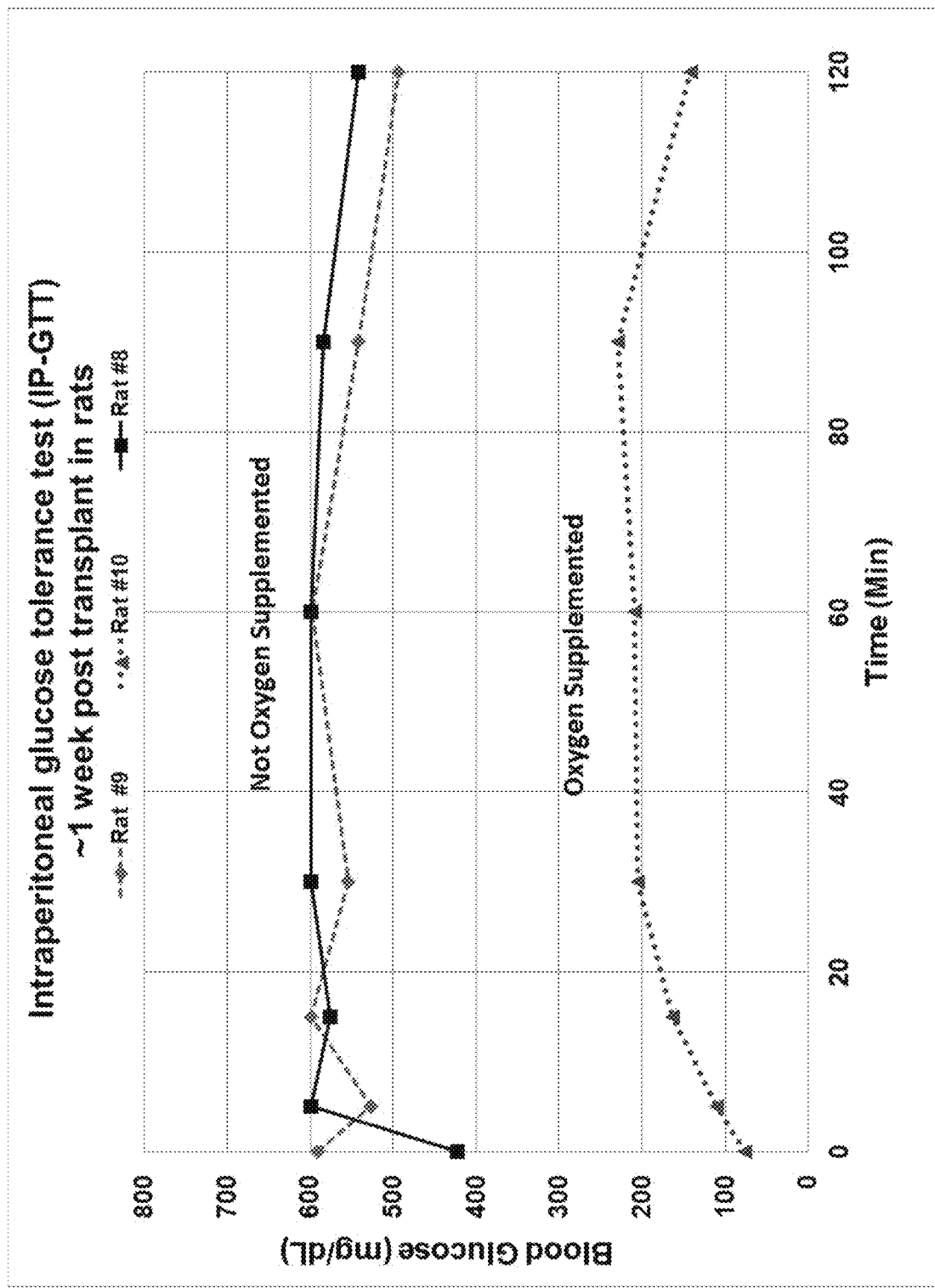
FIG. 13 is graph of experimental data of an intraperitoneal glucose tolerance test illustrating a rat's glucose control with and without oxygenation of the cellular implant.

Example 2: Demonstration of the Efficacy of Oxygenation With Respect to Glucose a Rat's Glucose Control. In a similar experiment as described above, the rats were tested at one week post-transplant for glucose tolerance by a standard IP-GTT test. The two rats without oxygen supplementation have high, diabetic glucose levels (~600 mg/dL). The rat with oxygen supplementation using the gas-treated cell implant system showed partial reversal of diabetes with a high normal reading (~200 mg/dL). FIG. 13 illustrates the experimental results from this test.

Example 3: Demonstration of the Efficacy of Oxygenation With Respect to Glucose a Rat's Glucose Control Over 14 Days. In another example, human (20,000 IEQ) or porcine (24,000 IEQ) islets are placed in 3 cm$^2$, 40 µl cell container with a cell chamber and one gas chamber with an external to the body electrochemical oxygen generator providing oxygen. This corresponds to a cell density of 6,600-8,000 islet equivalents per cm$^2$ surface area. The dose is less than 100 IEQ/g weight of recipient. The cell container includes a vascularizing membrane of expanded PTFE with pores greater than 3 µm bonded to an interior immunoisolating PTFE membrane with pores less than 0.5 µm. The cell containers are implanted subcutaneously in a diabetic rodent model. The membrane between the cell compartment and gas compartment is the same type of composite membrane (i.e. vascularizing membrane bonded to an immmunoisolating membrane) with the large pore membrane facing the gas container. The experimental cell containers are supplied with oxygen in at least 10 fold excess to the predicted metabolic consumption rate of the dose of islets. The control cell containers are not supplied with oxygen. Islets in cell containers supplied with oxygen maintain normal or near-normal blood glucose levels in the mammal in the range 50-200 mg/dl, while islets which are not supplied with oxygen have an impaired capacity for blood glucose regulation with glucose readings in the 300-500 mg/dl range. These results extend for at least fourteen days.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A system for gas treatment of a cell implant, the system comprising:
   (a) a gas generating subsystem, the gas generating subsystem comprising
      (i) an electrochemical device, the electrochemical device being configured to output a first gas, and
      (ii) a semipermeable membrane enclosure, the semipermeable membrane enclosure substantially completely encapsulating the electrochemical device, the semipermeable membrane enclosure being constructed to allow for passage therethrough of reactant needed by the electrochemical device; and
   (b) a cell containment subsystem, the cell containment subsystem comprising a first chamber configured to receive cells, the first chamber receiving the first gas outputted by the electrochemical device.

2. The system as claimed in claim 1 wherein the electrolyzer comprises a water electrolyzer.

3. The system as claimed in claim 2 wherein the water electrolyzer comprises a reservoir for holding a quantity of water.

4. The system as claimed in claim 1 wherein the first gas comprises one of gaseous oxygen and gaseous hydrogen.

5. The system as claimed in claim 1 wherein the electrochemical device is further configured to output a second gas and wherein the first gas comprises gaseous oxygen and the second gas comprises gaseous hydrogen.

6. The system as claimed in claim 5 wherein the first chamber receives the second gas outputted by the electrochemical device.

7. The system as claimed in claim 1 wherein the semipermeable membrane enclosure is further constructed to allow for penetration thereinto of microvasculature of a patient.

8. The system as claimed in claim 1 wherein the semipermeable membrane enclosure consists of a single layer.

9. The system as claimed in claim 8 wherein the semipermeable membrane enclosure has a pore size of no greater than about 0.5 µm and has a thickness of about 30 µm to about 50 µm.

10. The system as claimed in claim 1 wherein the semipermeable membrane enclosure comprises a plurality of layers.

11. The system as claimed in claim 10 wherein the semipermeable membrane enclosure comprises an inner layer and an outer layer, the inner layer having a pore size of no greater than about 0.5 µm, the outer layer having a pore size suitable for the penetration thereinto of microvasculature.

12. The system as claimed in claim 1 wherein the semipermeable membrane enclosure comprises a top portion and a bottom portion, the top portion and the bottom portion being joined together to define a space within which the electrochemical device is disposed.

13. The system as claimed in claim 1 wherein at least a portion of the first chamber is defined by a wall comprising at least one of an immuno-isolation membrane and a vascularizing membrane.

14. The system as claimed in claim 1 wherein the gas generating subsystem further comprises a first gas supply tube, the first gas supply tube having a first end and a second end, the first end of the first gas supply tube being fluidly coupled to the electrochemical device to receive the first gas from the electrochemical device.

15. The system as claimed in claim 14 wherein the cell containment subsystem further comprises a first delivery tube for use in conveying the first gas to cells in the first chamber, the first delivery tube having a first end, a second end, and a side wall, the first end of the first delivery tube being fluidly coupled to the second end of the first gas supply tube.

16. The system as claimed in claim 15 wherein the first delivery tube is disposed within the first chamber of the cell containment subsystem and is constructed for the first gas to be delivered to the first chamber through at least one of the second end of the first delivery tube and the side wall of the first delivery tube.

17. The system as claimed in claim 15 wherein the first chamber of the cell containment subsystem has a selectively permeable wall, the selectively permeable being permeable to gas but not to cells, and wherein the first delivery tube is disposed outside the first chamber proximate to the selectively permeable wall of the first chamber.

18. The system as claimed in claim 17 wherein the cell containment subsystem further comprises a second chamber, the second chamber being separated from the first chamber by the selectively permeable wall, the first delivery tube being formed in the second chamber against the selectively permeable wall as a supply channel.

19. The system as claimed in claim 17 wherein the first delivery tube is spaced apart from the selectively permeable wall of the first chamber by a distance of up to 5 mm.

20. The system as claimed in claim 1 wherein the first chamber comprises a cell supply port and wherein the gas generating subsystem and the cell containment subsystem are configured for implantation in a patient.

\* \* \* \* \*